United States Patent [19]

Ichikawa et al.

[11] 3,968,172

[45] July 6, 1976

[54] PROCESS FOR THE PREPARATION OF 2,4,6-TRIMETHYLPHENOL

[75] Inventors: Yataro Ichikawa; Yoshiyuki Yamanaka; Tatuyuki Naruchi; Osamu Kobayashi; Koichiro Sakota, all of Iwakuni, Japan

[73] Assignee: Teijin Limited, Osuha, Japan

[22] Filed: Oct. 2, 1973

[21] Appl. No.: 402,838

[52] U.S. Cl. ..................... 260/621 R; 260/612 D; 260/621 G
[51] Int. Cl.² ......................................... C07C 37/16
[58] Field of Search ............... 260/621 R, 624 C

[56] References Cited
UNITED STATES PATENTS

| | | | |
|---|---|---|---|
| 3,446,856 | 5/1969 | Hamilton | 260/621 R |
| 3,764,630 | 10/1973 | Van Sorge | 260/621 R |

Primary Examiner—Norman Morgenstern
Attorney, Agent, or Firm—Sherman & Shalloway

[57] ABSTRACT

A process for the preparation of 2,4,6-trimethylphenol by reacting a phenol of the formula (1) below,

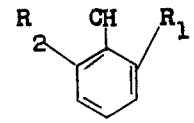

in which $R_1$ and $R_2$ each stands for hydrogen atom or methyl group with methanol at vapor phase, in the presence of a magnesium oxide-containing catalyst, to methylate the former, the characteristic features residing in that the reaction is performed at the temperatures ranging from 400° to 500°C., and the gaseous mixture composed essentially of the phenol and methanol is contacted with the catalyst at a flow rate not higher than 0.4/hour (sum weight in grams of the phenol and methanol/catalyst's weight in grams/hour).

20 Claims, No Drawings

PROCESS FOR THE PREPARATION OF 2,4,6-TRIMETHYLPHENOL

This invention relates to a process for the preparation of 2,4,6-trimethylphenol from a phenol of the formula (1) below:

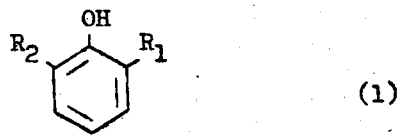

in which $R_1$ and $R_2$ each stands for hydrogen atom or methyl group. More particularly, the invention relates to a process for the direct preparation of 2,4,6-trimethylphenol of the formula (2) below:

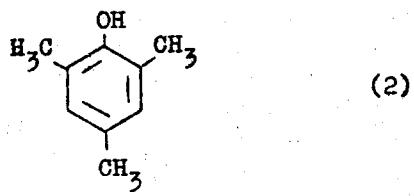

by reacting the aforesaid phenol with methanol at vapor phase, in the presence of a catalyst containing magnesium oxide.

An object of the invention is to provide a process for the direct preparation of 2,4,6-trimethylphenol from at least one of the phenols covered by the formula (1) at high yields.

Another object of the invention is to provide an economically advantageous process for the direct preparation of 2,4,6-trimethylphenol from particularly the phenol containing no methyl substituent group which can be expressed by the formula (1') below:

at a high conversion and high selectivity.

Still other objects and advantages of the invention will become apparent from reading the following specification.

Various methods are known in the past for the synthesis of 2,4,6-trimethylphenol, examples of which include:

1. introduction of a group such as —NH$_2$, —Cl—, —SO$_3$H, or the like, into mesitylene of the formula (3),

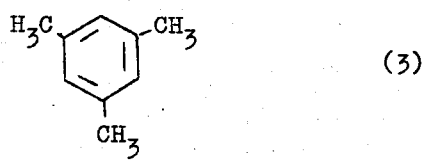

and subsequent conversion of the group to —OH:

2. reaction of the mesitylene with hydrogen peroxide, peracid, etc., in the presence of an acid such as HF, CF$_3$COOH, H$_2$SO$_4$, or CH$_3$COOH—H$_2$SO4; and 3. reaction of phenols with formaldehyde at liquid phase in the optional presence of dimethylamine to form trimethylol compound of the phenol or derivatives thereof, and subsequent hydrogenolysis thereof.

All of the above known processes, however, cannot be regarded industrially advantageous, because they require either expensive reaction reagent or complex operation steps.

Accordingly, if phenol of the formula (1') or the phenols containing one or two methyl groups at ortho positions[all of such phenols are collectively covered by the formula (1)], particularly the phenol containing no methyl substituent group, i.e., the phenol of formula (1'), could be directly converted through a single stage reaction to 2,4,6-trimethylphenol at high yields, industrial gain will be indeed great.

Preparation of ortho-cresol and/or 2,6-xylenol through the vapor phase reaction of phenol with methanol in the presence of magnesium oxide catalyst is also known from, for example, British Pat. No. 717,588, U.S. Pat. No. 3,446,856, its British equivalent, Pat. No. 1,034,500, and Chemical Abstract 70 19796b and 71 112619b.

However, all of the above-mentioned prior arts disclose the selective methylation of ortho-positions of unsubstituted phenol of the formula (1'). Consequently, according to those known methods, the yield of the compound containing methyl groups also at the para-positions of phenol, particularly 2,4,6-trimethylphenol, is at the best around 10 mol %. Thus one of the prior arts can constitute industrially practicable process for the preparation of 2,4,6-trimethylphenol.

Whereas, according to the invention 2,4,6-trimethylphenol can be obtained through a single stage reaction at a high yield, by reacting a phenol of the formula (1),

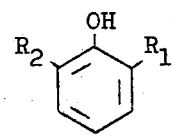

in which $R_1$ and $R_2$ each stands for hydrogen atom or methyl group, with methanol at vapor phase, in the presence of a catalyst containing magnesium oxide to effect methylation of the former, the characteristic features residing in that the reaction is performed at temperatures ranging from 400° to 500°C., and the gaseous mixture comprising at least phenol and methanol is contacted with the catalyst at a flow rate not greater than 0.4/hour [sum weight of phenol and methanol in grams/catalyst's grams/hour].

Hereinafter the invention will be explained in further details.

We discovered that in the preparation of 2,4,6-trimethylphenol through a single stage reaction at a high yield, i.e., by vapor phase methylation of phenols of formula (1), particularly the unsubstituted phenol of formula (1'), with methanol, A. selection of suitable temperature for the methylation reaction, B. selection of suitable flow rate of the starting gaseous mixture comprising the phenol and methanol to be fed into the reaction system including the catalyst bed [sum grams of phenol and methanol/catalyst grams/hour, i.e., 1/hour is used as the unit], and C. preferably, although not essential, the selection of specific magnesium oxide as the catalyst, are extremely important factors.

I. Reaction conditions:

As already stated, it is particularly important according to the present invention to control;

A. methylation reaction temperature, and

B. flow rate of phenol and methanol in the material gas [sum grams of phenol and methanol/catalyst grams/hour (unit; 1/hour)] within the suitable ranges.

The suitable temperature range for the methylation is 400° – 500°C., particularly 420° – 490°C. According to our studies, at the reaction temperatures close to the lower limit within the range of 400° – 500°C., p-methylation fails to progress at a satisfactory rate to reduce space time yield, and at the temperatures close to the upper limit, 2,6-methylation reaction becomes active and decomposition of methanol and the like also increases, to unexpectedly reduce the 2,4,6-trimethylphenol yield. Thus, at the reaction temperatures higher than 475°C., particularly than 500°C., extension of reaction time never results in the high yield formation of 2,4,6-trimethylphenol.

From the foregoing reasons, it is particularly advantageous to set the lower limit of the reaction temperature at 420°C., inter alia, 430°C., and the upper limit, at 475°C.

The essential starting materials of the invention are phenol and methanol, which are contacted with the solid catalyst containing magnesium oxide at vapor phase. The suitable ratio of the phenol to methanol in the starting gaseous mixture is such that, based on the theoretical mol number of the methyl group to be introduced per mol of the phenol to form 2,4,6-trimethylphenol, 0.5 – 5 molar times, particularly 1 – 3 molar times, the theoretical mol number of methanol is used per mol of the phenol.

According to the invention, the phenol and methanol to be fed into the reaction system containing the catalyst may be diluted with an inert gas. Any inert gas not detrimental to the methylation reaction can be used for that purpose, examples of useful gases including steam, hydrogen, nitrogen, argon, helium, and hydrocarbons stable under the reaction conditions, such as methane.

Such inert gases are used in the amount normal for the conventional vapor phase catalytic reaction. Use of an excessive amount should be avoided because such makes it difficult to secure sufficient contact time.

Among the above-mentioned inert gases, the most preferred is steam. The selectivity for 2,4,6-trimethylphenol can be improved by diluting the phenol and methanol with steam. In that case, it is more advantageous to dilute the phenol and methanol with the steam formed from the water not exceeding 10 molar times, preferably not exceeding 6 molar times, of the phenol employed.

According to the invention, the phenol and methanol mixture optionally containing the inert gas (which will be hereinafter referred to as the material gas) is fed into the reaction system containing the catalyst bed, at such a flow rate as will make the flow rate of the sum of phenol and methanol in the material gas [sum grams of phenol and methanol/catalyst grams/hour (unit: 1/hour)] not greater than 0.4 (1/hour), particularly from 0.01 – 0.2 (1/hour), inter alia, 0.04 – 0.15 (1/hour).

When the flow rate of phenol plus methanol exceeds the above upper limit, both the conversion of starting phenol and the yield of 2,4,6-trimethylphenol are reduced. Whereas, if the flow rate is low than the above lower limit, the yield per unit amount of the catalyst is reduced.

Performing the methylation of phenol thus controlling the flow rate of phenol plus methanol to the catalyst within the above-specified range and at the specified temperature range, it becomes possible to guide the reaction to essentially and selectively produce 2,4,6-trimethylphenol.

In order to afford the 2,4,6-trimethylphenol in good yield, it is desirable to carry out the methylation of phenol with methanol at a pressure (as absolute pressure) ranging from 0.5 to 20 atmospheres, preferably in a range of 1 to 16 atmospheres, more preferably in a range of 3 to 16 atmospheres.

II. Catalyst

According to the invention, phenol and methanol optionally diluted with an inert gas (the starting gaseous mixture) is contacted with a catalyst containing magnesium oxide, at vapor phase.

According to our studies, it is found that as the magnesium oxide to be used as the catalyst, particularly a. magnesium oxide which does not change color of both p-dimethylaminoazobenzene and 4-chloro-aniline serving as the indicators; and b. magnesium oxide which does not change color of both Methyl Red and 4-nitroaniline serving as the indicators, are advantageous.

The pKa's at which the specified indicators change colors, and the colors are as shown in Table 1 below.

Table 1

| Indicator | Change Point (pKa) | Color of Indicator Before Color Change | Color of Indicator After Color Change |
|---|---|---|---|
| p-Dimethylaminoazobenzene (dimethyl yellow) | 3.3 | yellow | red |
| p-Dimethylaminoazobenzene-carboxylic acid (Methyl Red) | 4.8 | yellow | red |
| 4-Nitroaniline (p-nitroaniline) | 18.4 | yellow | yellowish orange |
| 4-Chloroaniline (p-chloroaniline) | 26.5 | blank | pink |

As the catalyst to be employed in this invention, particularly the magnesium oxide which is shaped into optional forms such as pellet, granule, ring, block and spherical ball, and which has the pKa within the range satisfying the condition (a) above, still more particularly the condition (b), is suitable.

The measurement of pKa of solid magnesium oxide, particularly shaped magnesium oxide, using the indicators given in Table 1 can be effected, for example, by the following means for determining the acid-base strength.

Measurement of acid-base strength

The magnesium oxide to be used as the catalyst is heated in air at 450°C. for an hour, cooled under protection against moisture infiltration (for example, in a silica gel dessicator), and a minor portion of which (e.g., approx. 0.1 g) is put into refined benzene (e.g., approx. 5 cc). Into that sample a very minor amount (e.g. 4 to 5 drops) of a diluted benzene solution of the indicator (e.g., 0.1 wt. % benzene solution) is dropped, and state of color change after 40 hours' standing is observed with naked eye.

Therefore, that the magnesium oxide satisfies the condition (a) above signifies that it contains no acid strength of 3.3 or below as expressed by pKa (acidic substance) nor a strong base strength of 26.5 or above as pKa (strongly basic substance).

Similarly, the magnesium oxide satisfying the condition (b) neither contains the acid strength of pKa 4.8 or below, nor the strong base strength of pKa 18.4 or above. Such magnesium oxide satisfying the condition (a) or (b), particularly (b), is preferred for the process of this invention.

According to our studies, if a strong base strength higher than the pKa specified by the foregoing conditions, particularly (a), is present in the magnesium oxide, the 2,4,6-trimethylphenol yield during the early stage of the reaction (for example, the initial 6 hours or so after the reaction started) is reduced. Whereas, if an acid strength lower than the pKa specified in the foregoing conditions, particularly (a), is contained in the magnesium oxide, it is confirmed that the methylation of phenol at meta-positions concurrently takes place, to form meta-methylated derivatives as side-product. Consequently, not only the 2,4,6-trimethylphenol yield is reduced, but also the difficult separation of meta-methylated product becomes necessary. Meta-methylated phenols, e.g., 2,3,5-, 2,3,4-, and 2,3,4,6-methylated phenols, are extremely hard-separable from 2,4,6-trimethylphenol. It is especially desirable for the preparation of high purity 2,4,6-trimethylphenol, therefore, to use the magnesium oxide containing no acid strength of 3.3 or less pKa, or, more preferably, less than 4.8.

According to the invention, furthermore, the magnesium oxide serving as the catalyst may have the optional configuration, but should preferably be shaped, having the pore radius (r) ranging from 20 to 200 A, particularly from 30 to 150 A, and still more preferably, specific surface area of at least 15 m²/g, particularly from 20 to 200 m²/g, inter alia, from 40 to 100 m²/g.

Using the shaped magnesium oxide satisfying the above requirement on the pore radius (r), particularly both the requirements on average pore radius (r) and specific surface area, it becomes possible to further improve 2,4,6-trimethylphenol yield.

Incidentally, the pore radius (r) can be measured, for example, by pressurized mercury feed method, and the specific surface area, by BET method. Such measuring means are disclosed, for example, in the following literatures:

Mercury porosity measurement

H. L. Ritter, L. C. Drake, Ind. Eng. Chem. Anal. Ed, 17 782 (1945)

BET method

P. H. Emmett, Chem. Rev., 43 69 (1948)
P. E. Emmett, Catalysis, I, 31 (1954)
S. Brwnaver "The Adsorption of Gases and Vapors" Vol. 1, Physical Adsorption P271,317 (1954).

According to our studies, furthermore, it is discovered that for the high purity 2,4,6-trimethylphenol preparation at high yields, the ratio of basicity (k) in the magnesium oxide as expressed by the formula (4) below should advantageously range from 30 to 100%, particularly from 60 to 100%, inter alia, from 80 to 100%:

$$k = \frac{\text{basicity}}{\text{basicity} + \text{acidity}} \times 100\ (\%) \quad (4).$$

Thus the shaped magnesium oxide containing no acid strength of 3.3 or less pKa, preferably 4.8 or less pKa, as mentioned in the foregoing conditions (a) and (b), and furthermore having a ratio of basicity (k) within the above-specified range gives very favorable results when used as the catalyst.

The basicity and acidity necessary for determining the ratio of basicity (k) according to the formula (4) can be measured by the following methods.

Measurement of basicity (amount of base)

Similarly to the measurement of acid-base strength already described, the sample magnesium oxide is heated at 450°C. for an hour in air, and cooled to room temperature under protection against moisture infiltration. Approximately 2.1 g of the sample is placed in approximately 5 cc of refined benzene, and into which 0.1–N benzene solution of benzoic acid is titrated until Bromothymol Blue serving as the indicator changes color (color change point: pKa = 7.1) to determine the basicity. The particulars of this measuring method is disclosed in the below-identified literature.

ST. Malinowski and Azezepanska Journal of Catalysis 4, 324 – 331 (1965)
Jun-Ichiro Take, Nobuji Kikuchi, and Yukio Yoneda Journal of Catalysis 21, 164 – 170 (1971)
Stewart R. and O'Donnell, J. P. J. Am. Chem. Soc., 84, 493 (1962) Can. J. Chem., 42, 1681 (1964)

Measurement of acidity (amount of acid)

Approximately 0.1 g of the sample magnesium oxide which has been treated as above is placed in approximately 5 cc of refined benzene, and into the solution 0.1–N benzene solution of n-butylamine is dropped until Neutral Red as the indicator changes color (color change point: pKa = 6.8). The acidity can be determined by this tetration, particulars of which being disclosed in the below-identified literature.

O. Johnson J. Phys: Chem., 59, 827 (1955)
C. Walling J. Am. Chem. Soc., 72, 1164 (1950)
H. A. Bensi J. Am. Chem. Soc., 78, 5490 (1956)

Again according to the invention, up to 10% by weight, preferably up to 5% by weight, of the magnesium oxide as the catalyst may be replaced by a metallic compound specified below. Mixing of a suitable amount of such metallic compound produces such advantages as, for example, facilitation of magnesium oxide shaping, increasing the strength of so shaped product, and improving the catalytic ability by reducing the acidity of magnesium oxide.

As such metal compounds, oxides, hydroxides or inorganic acid salts of varius metals are used in suitable amounts which do not cause an extreme increase in the acid strength and acidity or basicity strength of the catalyst comprising magnesium oxide (MgO) and the metal compound or an extreme reduction in its surface area.

Examples of the metal oxides are oxides of alkaline earth metals such as calcium, strontium or barium, and those of zinc, titanium, zirconium, vanadium, chromium, tungsten or iron. The hydroxides include those of alkali metals such as lithium, sodium or potassium. Examples of the inorganic acid salts are carbonates, sulfates, phosphates, borates, silicates, aluminates, chromates, molybdates, tungstates, and vanadates of various metals, especially alkali metals and alkaline earth metals.

Of these metal compounds, at least one compounds selected from the group consisting of hydroxides, carbonates, phosphates, borates, silicates and aluminates of alkali metals, and oxides, carbonates, borates and phosphates of alkaline earth metals is preferred.

Various magnesium compounds which are convertible to magnesium oxide upon calcining, such as magnesium hydroxide or carbonate, basic magnesium carbonate, organic acid salts of magnesium such as formate, oxalate and acetate, magnesium nitrate, and the like, are calcined in vacuo, or in an inert gaseous atmosphere such as of nitrogen, helium, neon, argon, steam, or carbon dioxide, or in a molecular oxygen-containing gas (e.g., air) under the conditions suitable for this conversion to magnesium oxide.

The calcination temperature may range from 400° to 700°C., preferably from 450° to 650°C. Upon calcination the aforesaid various magnesium compounds at such temperature range, catalytically active magnesium oxide can be easily obtained.

Particularly the magnesium oxide catalyst formed by calcining magnesium hydroxide or basic magnesium carbonate in an atmosphere of molecular oxygen-containing gas is preferred.

It is furthermore discovered according to our studies that, when finely divided magnesium compound convertible to magnesium oxide upon calcination as above is compression moulded before the calcination for example, into cylindrical, pellet, ring, crushed, or spherical forms under the pressure not lower than 1000 ton/cm$^2$, preferably not lower than 500 ton/cm$^2$, and then calcined the catalyst having high activity and strength can be obtained.

If a magnesium compound which generates a gas, for example, carbon dioxide, under the calcination conditions, such as basic magnesium carbonate, is used as the starting material of the catalyst, however, it is preferably calcined in advance to be converted to magnesium oxide, and thereafter shaped, and calcined again if required, to provide the shaped catalyst for the subject process.

In the preparation of shaped magnesium oxide catalyst from the afore-specified magnesium compounds or magnesium oxide, conventional moulding assistant such as graphite, higher fatty acid such as stearic acid, water glass, or a high molecular compound such as cellulose acetate, carboxymethyl cellulose, and polyvinyl alcohol, may be added to facilitate the shaping operation and/or increase the strength of resulting shaped catalyst. Such a moulding assistant is preferably used in the amount of not more than 10% by weight, preferably 5% by weight, of the entire system, at the time of shaping.

When a metallic compound such as the aforenamed alkali metal or alkaline earth metal compound is added to magnesium oxide, the mixed catalyst can be prepared, for example, by the following methods:

Precipitation method

The metallic compound or a solution thereof is added to a solution (preferably aqueous solution) of a magnesium compound convertible to magnesium oxide upon calcination described as above to cause precipitation, and the precipitated solid is calcined.

Impregnation method

Pulverized or shaped magnesium compound as already specified is dipped inn a solution of the metallic compound, and then calcined.

Mixing method

Pulverized magnesium compound as above-named is uniformly mixed with the pulverized metallic compound, and the mixture is calcined.

By suitably selecting and combining the foregoing methods and conditions according to the invention, excellent magnesium oxide-containing shaped catalyst having the pKa value within the specified range in condition (a), particularly condition (b), the average pore radius (r) ranging 20 – 400 A, particularly 30 – 150 A, the specific surface area of at least 15 m$^2$/g, particularly from 20 – 200 m$^2$g, and, if necessary, the ratio of basicity (k) of 30 – 100%, particularly 60 – 100%, inter alia, 80 – 100%, can be formulated.

The process of this invention can be practiced by using such a catalyst, in an optional form such as a fixed bed or fluidized bed. Also any known apparatus suitable for conventional vapor phase catalytic reaction can be employed.

Regeneration of catalyst

When the specified phenol is methylated with methanol at vapor phase and at the temperature of 400° – 500°C. in the presence of a magnesium oxide-containing catalyst as above-described according to the invention, the activity of the catalyst gradually decreases after it has maintained its high activity for a few days.

According to our studies, the magnesium oxide-containing catalyst of which activity is reduced as the result of prolonged use in the specified methylation reaction can be reactivated (regenerated) by any of the following means, for example, i. contacting with molecular oxygen or a molecular oxygen-containing gas (oxidation treatment), ii. subjecting the used catalyst to the above oxidation treatment, and then contacting the same with water or steam (oxidation and subsequent water treatment) and iii. performing the oxidation treatment of (i) above simultaneously with the water treatment (simultaneous water treatment).

When the magnesium oxide-containing catalyst of which acitivity has been reduced is contacted with molecular oxygen or a molecular oxygen-containing gas at high temperatures, the carbon or carbide adhered onto the catalyst's surfaces is oxidized and removed. Thus the catalyst is again imparted with the high activity.

For the regeneration of used catalyst, the water treatment after the oxidation of (ii) above, and the simultaneous water treatment of (iii) are more effective than the oxidation treatment of (i). Obviously, the water treatment may be given before the oxidation, but the regenerating effect whereby achieved is substantially the same with that of the oxidation treatment of (i) alone.

The oxidation and water treatments for reactivation of used catalyst will be hereinafter explained in further details.

Oxidation treatment

The temperature at which the catalyst of reduced activity is contacted with molecular oxygen or a molecular oxygen-containing gas may be such that as will cause oxidation and substantial burning of the carbon or carbide adhering onto the catalyst's surfaces, which is normally 200°C. and above, preferably not lower than 300°C., particularly not lower than 350°C. The higher the contact temperature, the shorter may be the contact time, but excessively high temperatures cause reduction of catalyst's surface area, rendering the satisfactory regeneration of catalytic activity diffucult. Therefore, the upper limit of the contact temperature is 700°C., preferably 650°C., inter alia, 550°C.

The molecular oxygen used for the oxidation treatment may be pure oxygen, but more suitably is a molecular oxygen-containing gas composed of the pure oxygen diluted with an inert gas, in order to prevent rapid temperature rise caused by the combustion of the carbon or carbide adhering onto the catalyst's surfaces. For example, gaseous mixtures of molecular oxygen with such an inert gas as nitrogen, helium, argon, and the like, are used. Particularly air and a mixed gas formed by further diluting air with an inert gas as above-mentioned are preferred because of their easy availability.

The contact time should be long enough for the oxidation and substantial removal of the carbon or carbide adhering onto the surfaces of the catalyst. Although such is variable depending mainly on the contact temperature, normally several minutes to several hours are sufficient for the purpose. Generally speaking, when the temperature is relatively low, the used catalyst may be treated for many hours, but such prolonged oxidation reaction at temperatures as high as 600°C. or above may cause reduction in surface area of the catalyst and consequently, insufficient catalyst regeneration contrary to the purpose of the treatment.

Water treatment

It is preferred to regenerate the used catalyst by the aforesaid water treatment after the oxidation, or by simultaneous water treatment, rather than by the oxidation treatment alone, because by the former higher activities can be given to the regenerated catalyst. The suitable temperature at which the water treatment is performed after the oxidation treatment is at the lowest room temperature, preferably 100°C. or above. The upper limit can be advantageously set to be not higher than 650°C., preferably 400°C., inter alia, not higher than 250°C. The water treatment time normally ranges from several minutes to several tens of hours.

The simultaneous water treatment for the catalyst's regeneration can be effected by contacting the used catalyst with a gaseous mixture of molecular oxygen or a molecular oxygen-containing gas, and steam. The suitable temperature for that treatment is at the lowest 200°C., preferably 350°C. and above, the upper limit being 600°C, particularly 470°C.

The simultaneous oxidation and water treatment as above is industrially highly advantageous, and is the most preferred. Because, whereby not only is the catalyst activity regenerated substantially to the original level, but also the regeneration can be effected within the shorter time than that required for the consecutive practice of the oxidation and water treatments.

The regeneration of used catalysts can be effected in any form such as a fixed bed, fluidized bed or moving bed.

The magnesium oxide-containing catalyst can be thus used semi-permanently, by representing the above-described regeneration treatment whenever a reduction in the catalyst's activity is observed.

According to the invention, high purity 2,4,6-trimethylphenol can be produced through a single stage reaction at high yields, by methylating phenol with methanol at vapor phase, using the afore-specified magnesium oxide-containing catalyst, under the specified reaction conditions. Thus, it is made possible to convert phenol to 2,4,6-trimethylphenol with the yield of at least 50 mol %, and that of as high as 70 mol % or above under preferred conditions, as demonstrated also in the later given Examples. Furthermore, the object high purity 2,4,6-trimethylphenol can be easily separated and recovered from the methylation reaction product obtained upon the subject reaction, by, for example, distilling the product or cooling the same to crystallize 2,4,6-trimethylphenol.

As already mentioned, according to the invention 2,4,6-trimethylphenol can be produced with the high yields from unsubstituted phenol or the phenols containing one or two methyl substituent groups at ortho-positions. Whereas, it is also possible to produce high purity 2,4,6-trimethylphenol with high yields, by applying the identical conditions with those so far described to, for example, p-methylphenol or 2,4-dimethylphenol.

The 2,4,6-trimethylphenol obtained through the process of this invention is itself useful as, for example, an antioxidant. Not only that, it is useful also as an intermediate of perfume, various chemicals and pharmaceuticals. One example of such usage can be illustrated below.

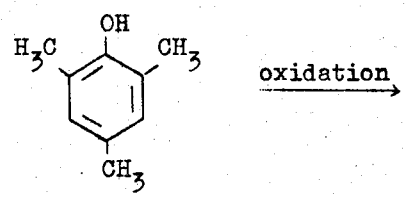

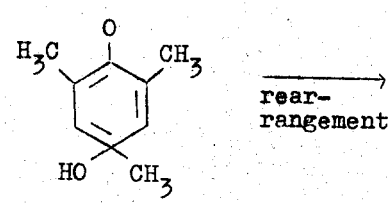

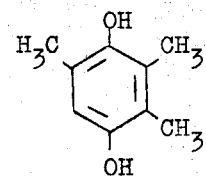

To wit, trimethylhydroquinone can be derived from the 2,4,6-trimethylphenol obtained by the present invention at a high yield according to the above reaction formula. The trimethylhydroquionone can be used as a starting material of vitamine E (tocopherol), upon condensation with, for example, phytol or iso-phytol.

Hereinafter the invention will be explained with reference to the working Examples, which should never be construed to limit the scope of the invention in any sense.

EXAMPLE 1

Preparation of catalyst

A suspension of 100 g of finely divided magnesium oxide in 800 ml of water was charged in an agitation tank, and stirred violently for 30 minutes. Whereupon the greatest part of the magnesium oxide was converted to magnesium hydroxide, which was recovered by filtration, dried at 100° – 120°C. for an overnight, and pressure-molded into each 5-mm thick tablets having a diameter of 6 mm, under a molding pressure of 5 – 6 t/cm².

The tablets were calcined for 3 hours at 600°C. in an electric oven, to provide a magnesium oxide catalyst. The calcination atmosphere was air.

Forty (40) g (74 ml) of the above catalyst was filled into 28-mm diameter quartz reaction tube. The space above the catalyst bed was packed with glass wool, and the tube was let stand upright. The catalyst bed was maintained at 450°C. by externally heating the tube with an electric heater.

The atmosphere inside the reaction tube was substituted with nitrogen gas, and thereafter a mixed solution of phenol and methanol (the mol ratio of methanol to phenol being 5.0) was fed into the tube from the top, at a flow rate of 5.0 ml (4.5 g) per hour through a quantitative pump. The reaction product leaving the reaction tube from the bottom was collected.

Six (6) hours after the reaction started, the fed phenol amounted to 9.9 g (105 mmol), and 18.2 g of the reaction product was obtained, most of which being in solid state. The reaction product was homogeneously dissolved in methanol and subjected to a quantitative analysis through gas chromatography. The results were as follows:

| | |
|---|---|
| 2,4-Xylenol | 0.077 g (0.63 mmol) |
| 2,6-Xylenol | 0.41 g (2.74 mmol) |
| 2,3,6-, 2,3,5-, and 2,4,5-trimethylphenols | 0.185 g (1.36 mmol) |
| 2,4,6-trimethylphenol | 10.8 g (79.20 mmol) |
| 2,3,4,6-tetramethylphenol | 0.41 g (2.74 mmol) |

The yields based on the fed phenol were, therefore, 2,4-xylenol 0.6%, 2,6-xylenol 3.5%, 2,3,6-, 2,3,5-, and 2,4,5-trimethylphenols 1.3%, 2,4,6-trimethylphenol 76%, and 2,3,4,6-tetramethylphenol 2.6%.

Likewise, the reaction product collected during the reaction of 6 to 24 hours was 62.4 g, and the yield of each component was as follows: 2,4-xylenol 0.5%, 2,6-xylenol 5.0%, 2,3,6-, 2,3,5-, and 2,4,5-trimethylphenols 1.1%, 2,4,6-trimethylphenol 83%, and 2,3,4,6-tetramethylphenol 2.1%.

The WHSV (i.e. the weight of phenol plus methanol fed per hour per unit weight of the catalyst) was 0.11 l/hr.

$$WHSV = \frac{\text{phenol plus methanol (wt/hr)}}{\text{catalyst weight (wt)}} (1/hr)$$

$$\text{Yield} = \frac{\text{formed 2,4,6-trimethylphenol (mol)}}{\text{fed phenol (mol)}} \times 100(\%)$$

EXAMPLE 2 AND CONTROL 1

In this Example the correlation of reaction temperature and WHSV with the reaction results is demonstrated.

The same catalyst employed in Example 1 was used. The WHSV was varied by changing the amount of the catalyst, while the mol ratio of methanol to phenol in the starting solution was always 5.0, and the feed rate was 5.0 ml (4.5 g) per hour.

The reaction and analysis methods were the same with those of Example 1. The reaction conditions and results were as given in Table 1 below, in which the reaction results were measured as to the reaction product collected during 6 – 24 hours' reaction.

From the results given in Table 1, it can be understood that the 2,4,6-trimethylphenol yield was the highest at 450°C., while at 550°C., 2,6-xylenol yield was high and that of 2,4,6-trimethylphenol was low. At the temperatures below 400°C., the yields of both 2,4,6-trimethylphenol and 2,6-xylenol were decreased.

Table 1

| Run No. | | Reaction temp. (°C.) | WHSV (hr⁻¹) | 2,4,6-Trimethylphenol yield (%) | 2,6-Xylenol yield (%) | 2,4-Xylenol yield (%) | Orthocresol yield (%) | Unreacted phenol (%) |
|---|---|---|---|---|---|---|---|---|
| Control | 1-1 | 550 | 0.22 | 1.4 | 29 | 3.2 | 32 | 9.4 |
| " | 1-2 | " | 0.50 | 12.5 | 71 | 1.2 | 4.8 | 2.8 |
| " | 1-3 | " | 1.1 | 11.0 | 77 | 0.5 | 4.6 | 3.1 |
| " | 1-4 | " | 2.2 | 5.7 | 68 | 0.2 | 10.2 | 7.1 |
| Example | 2-1 | 500 | 0.11 | 27 | 14 | 1.9 | 7.4 | 1.2 |
| " | 2-2 | " | 0.22 | 55 | 30 | 2.6 | 0.7 | 0.2 |
| Control | 1-5 | " | 0.50 | 39 | 48 | 0.8 | 1.1 | 2.7 |
| " | 1-6 | " | 1.1 | 18 | 64 | 0.4 | 3.5 | 1.8 |
| " | 1-7 | " | 2.2 | 1.9 | 26 | 0.9 | 26 | 28 |
| Example | 2-3 | 450 | 0.056 | 77 | 2.9 | 1.0 | 0 | 0 |
| " | 2-4 | " | 0.075 | 81 | 3.3 | 1.3 | 0 | 0 |
| " | 1 | " | 0.11 | 83 | 5.0 | 0.5 | 0 | 0 |
| " | 2-5 | " | 0.22 | 72 | 13 | 0.8 | 1.0 | 0 |
| Control | 1-8 | " | 0.50 | 6.9 | 21 | 3.5 | 26 | 29 |
| " | 1-9 | " | 1.1 | 1.3 | 7.3 | 1.7 | 21 | 40 |
| Example | 2-6 | 400 | 0.056 | 44 | 4.6 | 1.5 | 1.6 | 2.1 |
| " | 2-7 | " | 0.075 | 42 | 12.6 | 3.0 | 3.6 | 2.6 |
| " | 2-8 | " | 0.15 | 0.5 | 1.3 | 1.1 | 18 | 47 |

Table 1-continued

| Run No. | | Reaction temp. (°C.) | WHSV (hr⁻¹) | 2,4,6-Trimethylphenol yield (%) | 2,6-Xylenol yield (%) | 2,4-Xylenol yield (%) | Orthocresol yield (%) | Unreacted phenol (%) |
|---|---|---|---|---|---|---|---|---|
| Control | 1-10 | 375 | 0.056 | 1.5 | 2.0 | 1.7 | 17 | 28 |
| " | 1-11 | " | 0.11 | 1.3 | 4.0 | 2.3 | 21 | 38 |

EXAMPLE 3

This Example demonstrates the significance of the mol ratio of methanol to phenol.

Using the magnesium oxide catalyst prepared as in later appearing Example 9–4, the process of this invention was practiced similarly to Example 1, at the reaction temperature of 450°C., and pressure of 1 atm., the WHSV being 0.11 l/hr. The reaction results as to the products collected between 6 to 24 hours' reaction were as given in Table 2.

In the Table, the theoretical mol ratio is that of the methanol based on the theoretical mol number of methyl groups to be introduced per mol of phenol, for making 2,4,6-trimethylphenol.

Table 2

| Methanol/Phenol (mol ratio) | 10 | 8 | 7 | 6 | 5 | 4 | 3 | 2 |
|---|---|---|---|---|---|---|---|---|
| Theoretical Mol Ratio | 3.3 | 2.6 | 2.3 | 2.0 | 1.6 | 1.3 | 1.0 | 0.66 |
| Yield (%) Phenol | 0 | 0.2 | 0 | 0 | 0 | 0 | 3.5 | 8.4 |
| o-Cresol | 0 | 0.3 | 0 | 0 | 0 | 0.9 | 15 | 23 |
| 2,4-Xylenol | 0.1 | 0.7 | 0.8 | 0.8 | 1.0 | 2.7 | 6.6 | 8.2 |
| 2,6-Xylenol | 14 | 11 | 5.5 | 5.4 | 5.1 | 11 | 20 | 22 |
| 2,3,6-, 2,3,5-, and 2,4,5-Trimethylphenol | 0.9 | 1.3 | 0.7 | 0.8 | 0.9 | 0.7 | 0.2 | 0.1 |
| 2,4,6-Trimethylphenol | 62 | 68 | 76 | 79 | 81 | 74 | 34 | 16 |
| 2,3,4,6-Tetramethylphenol | 4.0 | 5.3 | 6.0 | 2.3 | 1.8 | 1.2 | 0.8 | 0 |
| Anisole | 0.2 | 1.2 | 0.6 | 0.5 | 0.5 | 1.1 | 1.5 | 2.7 |
| o- and p-Methylanisole | 0.7 | 0.4 | 0 | 0.3 | 0.1 | 0 | 0.3 | 0.2 |
| 2,6-Dimethylanisole | 3.2 | 0.6 | 0.5 | 0.3 | 0.4 | 0.2 | 0.2 | 0.1 |
| 2,4,6-Trimethylanisole | 7.6 | 3.0 | 2.3 | 1.1 | 0.9 | 0.7 | 0 | 0 |

EXAMPLE 4

In this Example, o-cresol, p-cresol, and 2,6-xylenol were used as the starting materials.

Instead of the phenol-methanol mixed solution, each of the above-mentioned starting materials was mixed with methanol to be reacted in the manner identical with Example 1.

The catalyst employed was the magnesium oxide prepared by the identical method under identical conditions with those described in the later-appearing Example 9–4.

The reaction conditions and results were as shown in Table 3 below, in which the reaction results were those obtained during 6 to 24 hours of the reaction.

Table 3

| Example No. | Startomg Material | WHSV (1/hr) | Reaction temp. (°C.) | Methanol Starting Material (mol ratio) | Theoretical Mol Ratio | o-Cresol p-Cresol | 2,4-Xylenol | 2,6-Xylenol | 2,4,6-Tri-methyl-phenol | 2,4,6-Tri-methyl-anisole | 2,3,4,6-Tetra-methyl-phenol |
|---|---|---|---|---|---|---|---|---|---|---|---|
| 4-1 | o-Cresol | 0.23 | 450 | 2.0 | 1.0 | 4.3 | 4.7 | 23.2 | 56.1 | 0 | 0.9 |
| 4-2 | " | 0.23 | 450 | 5.0 | 2.5 | 1.2 | 0.7 | 10.4 | 70 | 4.2 | 4.0 |
| 4-3 | " | 0.55 | 450 | 4.0 | 2.0 | 6.4 | 1.4 | 59 | 26 | 0 | 0 |
| 4-4 | " | 0.55 | 500 | 4.0 | 2.0 | 1.1 | 0.2 | 53 | 31 | 0 | 0.4 |
| 4-5 | p-Cresol | 0.23 | 450 | 4.0 | 2.0 | 0 | 3.0 | 2.0 | 81 | 0.7 | 1.0 |
| 4-6 | 2,6-Xylenol | 0.24 | 450 | 2.0 | 2.0 | 0.1 | 0.4 | 5.1 | 82 | 2.0 | 1.7 |
| 4-7 | " | 0.22 | 450 | 5.0 | 5.0 | 0.5 | 0.2 | 15.4 | 55 | 11.0 | 3.5 |
| 4-8 | " | 0.59 | 450 | 2.0 | 2.0 | 0.2 | 0.1 | 44 | 36 | 0 | 0.9 |
| 4-9 | " | 0.59 | 500 | 2.0 | 2.0 | 0.1 | 0.1 | 59 | 28 | 0 | 0.5 |

EXAMPLE 5

In this Example, the minor amounts of anisole and methyl-substituted anisoles by-produced of the subject process were contacted with the catalyst together with methanol, to be converted to 2,4,6-trimethylphenol in accordance with the invention.

Anisole, 2-methylanisole, 4-methylanisole, 2,4-dimethylanisole, 2,6-dimethylanisole and 2,4,6-trimethylanisole were each mixed with methanol, and the mixed solutions were reacted in the manner similar to Example 1, under the following reaction conditions: temperature, 450°C.; WHSV, 0.11 l/hr; and pressure, 1 atm. The reaction products obtained during 1 to 7 hours' reaction were analyzed. Thus determined compositions of phenols and anisoles (mol %) were as given in Table 4.

From the same Table it can be understood that the anisoles by-produced of the subject process are convertible to 2,4,6-trimethylphenol, when recirculated to the reaction system of the invention.

Table 4

| Example No. | Starting Material | Methanol Starting Material (mol ratio) | Compositions of Phenols and Anisoles in Reaction Product (mol %) | | | | | | | | |
|---|---|---|---|---|---|---|---|---|---|---|---|
| | | | Anisole | o-Cresol | 2-Methyl-anisole | 4-Methyl-anisole | 2,4-Xylenol | 2,4-Di-methyl-anisole | 2,6-Xylenol | 2,6-Di-methyl-anisole | 2,4,6-Tri-methyl-phenol | 2,4,6-Tri-methyl-anisole |
| 5-1 | Anisole | 5 | 33 | 12 | — | — | 15 | — | 13 | — | 24 | — |
| 5-2 | 2-Methyl-anisole | 5 | — | — | 38 | — | — | — | 20 | — | 28 | 5 |
| 5-3 | 4-anisole | 5 | — | — | — | 49 | — | — | — | — | 39 | 9 |
| 5-4 | 2,4-Di-metyl-anisole | 5 | — | — | — | — | — | 0.5 | 4 | — | 85 | — |
| 5-5 | 2,6-Di-methyl-anisole | 5 | — | — | — | — | — | — | 18 | 34 | 30 | 10 |
| 5-6 | 2,4,6-Tri-methyl-anisole | 5 | — | — | — | — | — | — | — | — | 80 | 4 |

EXAMPLE 6

This Example is to demonstrate the significance of reaction pressure and addition of water, in the run using phenol and methanol as the starting material.

A liquid mixture of phenol, methanol, and water was formed in a SUS 27 stainless steel reaction tube of 25 mm in inner diameter which was equipped with a thermometer and electric heater, and fed through a quantitative pump into an evaporator maintained at 230°C. to be evaporated. The vapor was led into a reaction tube of which temperature was maintained at the predetermined level.

The reaction product was collected by condensation at an intermediate reservoir maintained at approximately 90°C. The pressure was maintained at a predetermined level by feeding nitrogen gas into the reservoir or discharging therefrom a gaseous mixture of nitrogen and the gaseous reaction product.

The reaction product was subjected to the quantitative analysis similarly to Example 1.

The catalyst employed was that prepared through the identical procedures with those of Example 1. In all runs the mol ratio of methanol to phenol was 5.0, and other reaction conditions and results were as indicated in Table 5. In the same Table, WHSV is the weight of phenol plus methanol fed per hour per unit weight of the catalyst (weight of water being excluded). In Examples 6-2 and 6-4, nitrogen gas was used instead of water.

From the results given in Table 5, it is confirmed that under the reaction pressure of 1 atm. and temperature of 450°C., addition of water or nitrogen gas achieves substantially no appreciable effect as to STY of 2,4,6-trimethylphenol, but when the added amount of water or nitrogen is 2 molar times the phenol, water gives a better result, and also that the catalyst's activity lasts with better stability in the presence of water or nitrogen gas. It can be furthermore understood that, under an elevated pressure and large WHSV, the STY of 2,4,6-trimethylphenol increases, and the addition of water is effective for sustaining the catalyst's activity.

Incidentally, "STY" of 2,4,6-trimethylphenol is the mol number of 2,4,6-trimethylphenol obtained per hour per 1 kg of the catalyst.

Table 5

| Example No. | Reaction Pressure (atm.) | Reaction Temp. (°C.) | WHSV (1/hr) | H₂O/PhOH (mol ratio) | Yield (%) and STY (mol/kg.hr) of 2,4,6-Trimethyl-phenol | Reaction Time (hr.) | | | | | |
|---|---|---|---|---|---|---|---|---|---|---|---|
| | | | | | | 1-3 | 3-6 | 6-15 | 15-24 | 24-34 | 34-44 |
| 6-1 | 1 | 450 | 0.11 | 2 | Yield | 51 | 73 | 67 | 63 | 61 | 62 |
| | | | | | STY | 0.22 | 0.32 | 0.29 | 0.27 | 0.26 | 0.27 |
| 6-2 | 1 | 450 | 0.11 | N₂ 2 | Yield | 54 | 68 | 62 | 57 | 53 | 49 |
| | | | | | STY | 0.24 | 0.29 | 0.27 | 0.25 | 0.23 | 0.21 |
| 6-3 | 1 | 450 | 0.11 | 10 | Yield | 53 | 50 | 45 | 41 | 36 | |
| | | | | | STY | 0.23 | 0.22 | 0.19 | 0.18 | 0.16 | |
| 6-4 | 1 | 450 | 0.11 | N₂ 10 | Yield | 57 | 56 | 50 | 47 | 42 | |
| | | | | | STY | 0.25 | 0.24 | 0.22 | 0.20 | 0.18 | |
| 6-5 | 8 | 450 | 0.23 | 3 | Yield | 63 | 67 | 62 | 60 | 57 | |
| | | | | | STY | 0.57 | 0.61 | 0.56 | 0.54 | 0.52 | |
| 6-6 | 8 | 490 | 0.74 | 6 | Yield | 50 | 56 | 17 | | | |
| | | | | | STY | 1.45 | 1.63 | 0.49 | | | |
| 6-7 | 8 | 550 | 1.20 | 6 | Yield | 62 | 25 | 5 | | | |
| | | | | | STY | 2.93 | 1.18 | 0.24 | | | |
| 6-8 | 10 | 470 | 0.22 | 6 | Yield | 36 | 54 | 57 | 56 | 54 | 45 |
| | | | | | STY | 0.31 | 0.47 | 0.49 | 0.48 | 0.47 | 0.39 |
| 6-9 | 10 | 450 | 0.45 | 10 | Yield | 45 | 42 | 26 | | | |
| | | | | | STY | 0.80 | 0.74 | 0.46 | | | |
| 6-10 | 14 | 470 | 0.44 | 6 | Yield | 50 | 53 | 44 | 33 | 24 | |
| | | | | | STY | 0.87 | 0.92 | 0.76 | 0.57 | 0.42 | |
| 6-11 | 16 | 450 | 0.63 | 0 | Yield | 25 | 14 | | | | |
| | | | | | STY | 0.62 | 0.35 | | | | |
| 6-12 | 20 | 430 | 0.31 | 6 | Yield | 46 | 45 | 43 | 40 | 37 | 35 |

Table 5-continued

| Example No. | Reaction Pressure (atm.) | Reaction Temp. (°C.) | WHSV (1/hr) | H₂O/PhOH (mol ratio) | Yield (%) and STY (mol/kg.hr) of 2,4,6-Trimethyl-phenol | Reaction Time (hr.) | | | | | |
|---|---|---|---|---|---|---|---|---|---|---|---|
| | | | | | | 1-3 | 3-6 | 6-15 | 15-24 | 24-34 | 34-44 |
| | | | | | STY | 1.33 | 1.31 | 1.25 | 1.16 | 1.08 | 1.02 |

EXAMPLE 7

The significance of reaction pressure and addition of water is again demonstrated in this Example, using phenol and methanol as the starting material.

The experiments were run in the identical manner with Example 6, and the reaction conditions and results were as given in Table 6.

The catalyst used was a commercial magnesia in the form of each 3-mm diameter and 3-mm thick tablets, having a specific surface area of 20 m²/g, pore size distribution pore radius of 50 – 140 A, pore volume of 0.16 cc/g, and an acid-base strength (pKa) of 4.8 – 17.2.

The blue or green-colored catalyst was titrated with a 0.1-N refined benzene solution of benzoic acid until its color changed to yellow, consuming approximately 3 days, and from the result the amount of benzoic acid required for the titration per gram of the catalyst was calculated, which was expressed as the basicity by the unit of mmol/g. Therefore, the basicity denotes the amount of base on the catalyst surface per gram thereof, said catalyst having a pKa of at least 7.1

Measurement of acidity

Using Neutral Red as the indicator instead of Bromthimol Blue, the red-colored catalyst was titrated with a 0.1-N refined benzene solution of n-butylamine until its

Table 6

| Example No. | Reaction Pressure (atm.) | Reaction Temp. (°C.) | WHSV (1/hr) | H₂O/PhOH (mol ratio) | Yield (%) and STY (mol/kg.hr) of 2,4,6-Trimethyl-phenol | Reaction Time (hr.) | | | | |
|---|---|---|---|---|---|---|---|---|---|---|
| | | | | | | 1-3 | 3-6 | 6-15 | 15-24 | 24-34 |
| 7-1 | 0 | 450 | 0.11 | 0 | Yield | 58 | 63 | 62 | 58 | 55 |
| | | | | | STY | 0.25 | 0.27 | 0.26 | 0.25 | 0.23 |
| 7-2 | 6 | 470 | 0.11 | 6 | Yield | 65 | 65 | 54 | 43 | 40 |
| | | | | | STY | 0.28 | 0.28 | 0.23 | 0.18 | 0.17 |
| 7-3 | 10 | 470 | 0.21 | 6 | Yield | 63 | 67 | 63 | 61 | 49 |
| | | | | | STY | 0.52 | 0.55 | 0.52 | 0.50 | 0.40 |
| 7-4 | 12 | 450 | 0.21 | 6 | Yield | 67 | 69 | 62 | 59 | 52 |
| | | | | | STY | 0.55 | 0.57 | 0.51 | 0.48 | 0.43 |
| 7-5 | 20 | 450 | 0.52 | 6 | Yield | 36 | 27 | 10 | 6.8 | |
| | | | | | STY | 0.73 | 0.55 | 0.20 | 0.14 | |

EXAMPLE 8

The correlation of acid-base strength, basicity, and acidity of catalyst with the catalyst's activity is examined in this Example.

Measurement of acid-base strength:

The catalyst was treated in an electric oven for an hour at 450°C. in air under normal pressure, immediately transferred into a desiccator containing silica gel as a drying agent, and allowed to cool off to room temperature. Approximately 0.1 to 0.15 g of the catalyst was thrown into 5 cc of refined benzene, and pulverized in situ with a glass rod. Into the system 4 drops of a 0.1 wt. % refined benzene solution of the specified indicator was added and shaken. After 40 hours of subsequent standing, the color change in the catalyst was judged with naked eye, to determine the acid-base strength.

Measurement of basicity

Similarly to the measurement of acid-base strength, the catalyst was heated at 450°C. for an hour, and 0.1 – 15 g of the catalyst was precisely measured with a micro-chemical balance. The catalyst was pulverized in 5 cc of refined benzene, into which 4 drops of a 0.1 wt. % refined benzene solution of Bromthymol Blue as the indicator were added.

color changed to yellow, in the manner similar to the basicity measurement. Thus the amount of n-butylamine required for the titration was determined and expressed by the unit of mmol/g as the acidity. Therefore, the acidity refers to the amount of acid on the surface of 1 g of the catalyst having a pKa of no higher than 6.8.

The color change of employed indicators and pKa

| Indicator | Color Change Point (pKa) | Neutrality | Basicity |
|---|---|---|---|
| 4-Chloroaniline | 26.5 | blank | pink |
| 4-Nitroaniline | 18.4 | yellow | yellowish orange |
| 4-Chloro-2-nitro-aniline | 17.2 | yellow | orange |
| 2,4-dinitroaniline | 15.0 | yellow | purple |
| Bromthymol Blue | 7.1 | yellow | blue |

| Indicator | Color Change Point (pKa) | Acidity | Neutrality |
|---|---|---|---|
| Neutral Red | 6.8 | red | yellow |
| Methyl Red | 4.8 | red | yellow |
| Dimethyl Yellow | 3.3 | red | yellow |
| Benzene azodiphenyl-amine | 1.5 | violet | yellow |
| Dicinnamalacetone | −3.0 | red | yellow |

The following literatures were referred to for the measurement of acid-base strength, acidity and basicity:

(Concerning acidity)

O. Johnson, J. Phys. Chem. 59, 827 (1955)
C. Walling, J. Am. Chem. Soc. 72, 1164 (1950)
H. A. Benesi, J. Am. Chem. Soc. 78, 5490 (1956)

(Concerning basicity)

S. T. Malinowski and Szezepanska, *Journal of Catalysis*, 4, 324 - 331 (1965)
Jun-ichiro Take, Nobuji Kikuchi, & Yukio Yoneda, *Journal of Catalysis*, 21, 164 - 170 (1971)
R. Stewart & J. P. O'Donnell, J. Am. Chem. Soc. 84, 493 (1962) Can. J. Chem. 42, 1681 (1964)

Preparation of Catalyst

The catalyst of Example 8-1:

Into a solution formed of 218 g (5.45 mols) of sodium hydroxide dissolved in 5 liters of water which was maintained at 50° - 60°C., another solution of 636 g (2.48 mols) of magnesium nitrate ($Mg(NO_3)_2 \cdot 6H_2O$) in 4 liters of water was dropped under stirring, consuming approximately an hour. The precipitate of magnesium hydroxide whereupon formed was separated by filtration after the system was allowed to stand for an overnight. The precipitate was again dispersed in 5 liters of water and filtered. After repeating the dispersion-filtration procedure three times, the precipitate was dried for a night at 100° - 120°C., and pressure-molded into tablets of each 6 mm in diameter and 5 mm in thickness, similarly to Example 1. The tablets were calcined in an electric oven in the normal atmosphere, for 3 hours at 550°C.

The catalyst of Example 8-2:

The catalyst of above Example 8-1 was further calcined for additional 6 hours at 600°C.

The catalyst of Example 8-3:

Similarly to Example 1, magnesium oxide was converted to magnesium hydroxide, which was pressure-molded again similarly to Example 1. No calcining treatment was given.

The catalyst of Example 8-4:

The tablets of magnesium hydroxide of Example 8-3 were calcined for an hour at 800°C.

The catalyst of Example 8-5:

The magnesium hydroxide tablets of Example 8-3 were calcined for 3 hours at 600°C., and further for an hour at 1,000°C.

The catalyst of Example 8-6:

One-hundred (100)g of magnesium oxide powder was violently mixed with 800 ml of an aqueous solution containing 1 g of sodium hydroxide, so that the greatest part of the magnesium oxide was converted to magnesium hydroxide. Then the suspension was evaporated to dryness under thorough stirring, and further dried for an overnight at 100° - 120°C. The subsequently pressure-molded catalyst was calcined for 3 hours at 550°C.

The catalyst of Example 8-7:

One-hundred (100) g of magnesium oxide powder was violently mixed with 800 ml of water for 20 minutes so that the greatest part of the magnesium oxide was converted to magnesium hydroxide. Then 50 g of 20 wt. % silica mol was added to the system followed by 20 minutes' violent stirring. The system was subsequently filtered. Thus recovered solid was dried at 100° - 120°C. for an overnight, pressure-molded, and calcined at 550°C. for 3 hours. Thus obtained catalyst had such a composition that the silica ($SiO_2$) content was 10 wt % to the magnesium oxide (weight ratio: 0.10).

The catalyst of Example 8-8:

A catalyst was prepared from 50 g of magnesium oxide powder and 250 g of 20 wt % silica sol, in the manner similar to Example 8-7. The composition of the catalyst was such that the silica ($SiO_2$) content was 50 wt % to the magnesium oxide (weight ratio: 1.0).

The catalyst of Example 8-9:

A catalyst was prepared from 50 g of magnesium oxide powder and 500 g of 10 wt % alumina sol, in the manner similar to Example 8-7. The composition of the catalyst was such that the alumina ($Al_2O_3$) content to the magnesium oxide was 50 Wt. % (weight ratio: 1.0).

The results of measuring the acid-base strength basicity and acidity of the foregoing catalysts were as given in Table 7.

The foregoing catalysts were used in the reaction according to the invention with the results as shown in Table 8 below. In all runs, the reaction temperature was 450°C., WHSV was 0.11 l/hr., and the mol ratio of methanol to phenol was 5.0.

From Tables 7 and 8, it can be seen that in Examples 8-1 and 8-3 wherein the base strength of 26.5 (pKa) was observed, decomposition of reaction product took place and presence of phenol and methylated phenol was hardly traceable in the system.

The strong base strength disappeared upon calcining the catalyst, and the catalyst was given an appropriate catalytic ability.

With the catalyst in which the acidity is higher compared with the basicity (that having a small k in Table 7), side-production of meta-methylated phenols, such as 2,3,6-trimethylphenol, 2,5,6-trimethylphenol, 3,4,6-trimethylphenol, and 2,3,4,6-tetramethylphenol, increases. Such a catalyst having the high acidity was obtained when the calcining temperature of the magnesium oxide catalyst was excessively high, or when an additive or additives which impart acidity to magnesium oxide were contained in the catalyst.

Table 7

| Ex. No. | Method of Preparation or composition | Calcinating conditions °C. | hr. | Acid and Base Strength (pKa) 26.5 | 18.4 | 17.2 | 15.0 | 7.1 | 4.8 | 3.3 | 1.5 | 3.0 | B m mol/g | A m mol/g | K | S m²/g | V cc/g | r A |
|---|---|---|---|---|---|---|---|---|---|---|---|---|---|---|---|---|---|---|
| 8-1 | Magnesium hydroxide obtained | 550 | 3 | O | O | O | O | O | Δ | X | X | X | 1.28 | O | 100 | 67 | 0.55 | 99 |
| 8-2 | from magnesium nitrate and sodium hydroxide | 550 600 | 3 6 | X | O | O | O | O | Δ | X | X | X | — | — | — | 53 | — | — |

Table 7-continued

| Ex. No. | Method of Preparation or composition | Calcinating conditions °C. | hr. | Acid and Base Strength (pKa) | | | | | | | | B m mol/g | A m mol/g | K | S m²/g | V cc/g | r A |
|---|---|---|---|---|---|---|---|---|---|---|---|---|---|---|---|---|---|
| | | | | 26.5 | 18.4 | 17.2 | 15.0 | 7.1 | 4.8 | 3.3 | 1.5 | 3.0 | | | | | | |
| 8-3 | Magnesium hydroxide obtained from magnesium oxide and water | Calcinating | | O | O | O | O | O | O | O | X | X | 1.37 | 0.14 | 91 | 116 | — | — |
| 1 | | 600 | 3 | X | X | X | O | O | Δ | X | X | X | 1.80 | 0.20 | 90 | 75 | — | — |
| 8-4 | | 800 | 3 | X | X | X | X | O | O | Δ | X | X | 0.17 | 0.20 | 46 | 24 | — | — |
| 8-5 | | 600 1000 | 3 1 | X | X | X | X | O | O | O | X | X | 0.11 | 0.18 | 38 | 11 | 0.67 | 1180 |
| 8-6 | NaOH/MgO 0.01 (wt. ratio) | 550 | 3 | X | Δ | O | O | O | Δ | X | X | X | 1.0 | O | 100 | 92 | — | — |
| 8-7 | SiO₂/MgO 0.10 (wt. ratio) | 550 | 3 | X | X | Δ | O | O | O | O | X | X | 0.30 | 0.28 | 52 | 130 | — | — |
| 8-8 | SiO₂/MgO 1.0 (wt. ratio) | 550 | 3 | X | X | Δ | O | O | O | O | X | X | 0 | 0.67 | O | 166 | — | — |
| 8-9 | Al₂O₃/MgO 1.0 (wt. ratio) | 550 | 3 | X | X | X | X | O | O | O | O | X | 0 | 0.70 | O | 76 | — | — |

The acid and base strengths are indicated by the pKa's corresponding to those of the indicators, O denoting that the color change was observed, Δ, judgment of color change was difficult, and X, no color change was recognized.

B stands for basicity.

A stands for acidity.

k is calculated as B/A+B × 100

S denotes specific surface area.

V shows the volume of pores having the radii of 16 – 4400 A.

r shows the average pore radius of the pores having the radii ranging from 16 to 4400 A.

dispersed in 5 liters of water and filtered. Repeating the dispersion filtration procedures three times, the precipitate was dried at 100° – 120°C. for a night, and then pressure-molded into the tablets of each 6 mm in diameter and 5 mm in thickness, under a pressure of 5 – 6 t/cm². The tablets were calcined in an electric oven in the normal atmosphere, at 550°C. for 3 hours.

Example 9–2

Commercial magnesium hydroxide was pressure-molded similarly to above Example 9–1, and the tablets were calcined in an electric oven at 400°C. for 3 hours.

Example 9–3:

Commercial magnesium oxide tablets were used.

Table 8

| Ex. No. | Yield During 0 – 6 Hours of Reaction (%) | | | | | | Yields During 6 – 24 Hours of Reaction (%) | | | | | |
|---|---|---|---|---|---|---|---|---|---|---|---|---|
| | Phenol | 2,4-Xylenol | 2,6-Xylenol | 2,4,6-Tri-methyl-phenol | 2,3,6-, 2,5,6, and 3,4,6-Tri-methyl-phenol | 2,3,4,6-Tetra-methyl-phenol | Phenol | 2,4-Xylenol | 2,6-Xylenol | 2,4,6-Tri-methyl-phenol | 2,3,6-, 2,5,6, and 3,4,6-Tri-methyl-phenol | 2,3,4,6-Tetra-methyl-phenol |
| 8-1 | O | O | O | O | O | O | O | O | O | O | O | O |
| 8-2 | O | 2.0 | 9.1 | 27 | 0.8 | 0.2 | O | 1.2 | 22 | 35 | 0.4 | 0.1 |
| 8-3 | O | O | O | 2.0 | O | O | 0.1 | O | 0.5 | 67 | 0.8 | 2.5 |
| 1 | O | 0.6 | 3.5 | 76 | 1.3 | 2.6 | O | 0.5 | 5.0 | 83 | 1.1 | 2.1 |
| 8-4 | O | 3.9 | 22 | 45 | 2.5 | 5.4 | O | O | 17 | 32 | 1.8 | 4.4 |
| 8-5 | O | 7.0 | 41 | 20 | 1.6 | 0.7 | 5.5 | 18 | 43 | 13 | 0.4 | 0.3 |
| 8-6 | O | 0.2 | 4.3 | 78 | 1.8 | 0.9 | O | 0.7 | 14 | 71 | 0.8 | 0.2 |
| 8-7 | O | O | 0.8 | 36 | 3.4 | 15 | O | O | 1.8 | 49 | 4.1 | 16 |
| 8-8 | 0.7 | O | 3.4 | 3.9 | 16 | 3.6 | 0.2 | O | 6.9 | 9.7 | 13 | 5.8 |
| 8-9 | 0.8 | O | 2.4 | 3.2 | 12 | 3.2 | 0.2 | O | 4.2 | 12 | 11 | 9.6 |

EXAMPLE 9

This Example demonstrates the correlation of pore size distribution in the catalyst with catalytic activity.

Preparation of catalyst

Example 9–1:

3.5 Liters of an aqueous solution was formed by adding water to 452 g of 28% aqueous ammonia, and into which 1.5 liters of another aqueous solution containing 636 g of magnesium nitrate [Mg(NO₃)₂.6H₂O] (2.48 mols) was dropped under stirring at room temperature, consuming approximately one hour. The system was allowed to stand at room temperature for a night, and then filtered. The separated precipitate was Example 9–4:

The magnesium hydroxide obtained from magnesium oxide powder and water similarly to Example 1 was pressure-molded into tablets, and calcined at 550°C. for 6 hours.

Example 9–5:

The magnesium oxide tablets having a specific surface area of 64 m²/g and a pore volume of 0.57 cc/g (pore size distribution: 20 – 200 A) were calcined at 600°C. for 40 hours in an electric oven.

Example 9–6:

The same magnesium hydroxide tablets as employed in Example 8—3 were calcined at 700°C. for 6 hours in an electric oven.

Example 9–7:

The same magnesium hydroxide tablets as formed in Example 8–3 were calcined at 800°C. for 6 hours in an electric oven.

Example 8–5:

As already specified, the magnesium hydroxide tablets of Example 8–3 were calcined at 600°C. for 3 hours, and then at 1,000°C. for an hour in an electric oven.

Measurement of pore size distribution

The pore sizes were measured by mercury porosity measurement, using a "Porosimeter" No. 5 - 7125B (60,000 psi) (product of AMINCO) according to the itself accepted practice. The pore radii were measured down to 16 A, pores of less sizes being excluded from the calculation of pore size distribution.

According to the conventional practice, the interrelation of pore radius (r) and pore volume (V) were determined, first from the correlation of the pressure with pore volume, and then from that of the pressure with pore radius. The results were as shown in Table 9 below.

In Examples 9–6 and 9–7, and 8–5, pores having the radii greater than 4400 A were present, but the measured values shown are those as to the pores having the radii within the range of 16 – 4400 A. This statement also applies to the given values of pore volume and average pore radius.

Measurement of specific surface area

The specific surface area of the catalyst was measured in accordance with an improved BET method, using Perkin-Eisner Shell Model 212D Sorptometer.

Table 9

| Pore Radius (r) A | Example 9-1 V (cc/g) | Example 9-1 dV (cc/g) | Example 9-2 V (cc/g) | Example 9-2 dV (cc/g) | Example 9-3 V (cc/g) | Example 9-3 dV (cc/g) | Example 9-4 V (cc/g) | Example 9-4 dV (cc/g) | Example 9-5 V (cc/g) | Example 9-5 dV (cc/g) |
|---|---|---|---|---|---|---|---|---|---|---|
| 16 | 0 | 0 | 0 | 0.102 | 0 | 0 | 0 | 0.030 | | |
| 25 | 0 | 0.02 | 0.102 | 0.062 | 0 | 0 | 0.030 | 0.075 | | |
| 35 | 0.02 | 0.08 | 0.164 | 0.018 | 0 | 0 | 0.105 | 0.050 | | |
| 45 | 0.11 | 0.08 | 0.182 | 0.013 | 0 | 0.006 | 0.155 | 0.035 | | |
| 55 | 0.19 | 0.07 | 0.195 | 0.007 | 0.006 | 0.034 | 0.190 | 0.035 | 0 | 0.006 |
| 65 | 0.26 | 0.035 | 0.202 | 0.015 | 0.040 | 0.033 | 0.225 | 0.035 | 0.006 | 0.022 |
| 75 | 0.295 | 0.013 | 0.217 | 0.007 | 0.073 | 0.030 | 0.260 | 0.040 | 0.028 | 0.027 |
| 85 | 0.308 | 0.005 | 0.224 | 0.028 | 0.103 | 0.028 | 0.300 | 0.040 | 0.055 | 0.035 |
| 95 | 0.313 | 0.003 | 0.252 | 0.018 | 0.131 | 0.014 | 0.340 | 0.042 | 0.090 | 0.048 |
| 105 | 0.316 | 0.007 | 0.270 | 0.040 | 0.145 | 0.012 | 0.382 | 0.035 | 0.138 | 0.092 |
| 115 | 0.323 | 0.007 | 0.310 | 0.057 | 0.157 | 0.006 | 0.417 | 0.028 | 0.230 | 0.095 |
| 125 | 0.330 | 0 | 0.367 | 0.020 | 0.163 | 0.002 | 0.445 | 0.016 | 0.335 | 0.075 |
| 135 | 0.330 | 0 | 0.387 | 0.013 | 0.165 | 0 | 0.461 | 0.017 | 0.410 | 0.035 |
| 145 | 0.330 | 0 | 0.400 | 0.014 | 0.165 | 0 | 0.478 | 0.012 | 0.445 | 0.017 |
| 155 | 0.330 | 0 | 0.414 | 0.008 | 0.165 | 0 | 0.490 | 0.010 | 0.462 | 0.013 |
| 165 | 0.330 | 0 | 0.422 | 0.006 | 0.165 | 0 | 0.500 | 0.005 | 0.475 | 0.011 |
| 175 | 0.330 | 0 | 0.428 | 0.004 | 0.165 | 0 | 0.505 | 0.005 | 0.486 | 0.009 |
| 185 | 0.330 | | 0.432 | 0.003 | 0.165 | 0 | 0.510 | 0.006 | 0.495 | 0.005 |
| 195 | | | 0.435 | 0 | 0.165 | | 0.516 | 0.004 | 0.500 | 0.005 |
| 205 | | | 0.435 | 0 | | | 0.520 | 0.005 | 0.505 | 0.005 |
| 215 | | | 0.435 | 0 | | | 0.525 | 0.003 | 0.510 | 0.002 |
| 225 | | | 0.435 | | | | 0.528 | 0.004 | 0.512 | 0.002 |
| 235 | | | | | | | 0.532 | 0.003 | 0.514 | 0.001 |
| 245 | | | | | | | 0.535 | 0 | 0.515 | 0.001 |
| 255 | | | | | | | 0.535 | 0 | 0.516 | 0.001 |
| 265 | | | | | | | 0.535 | 0 | 0.517 | 0.001 |
| 275 | | | | | | | 0.535 | 0 | 0.518 | 0.001 |
| 285 | | | | | | | 0.535 | 0 | 0.518 | 0 |
| 295 | | | | | | | 0.535 | | 0.518 | 0 |
| 305 | | | | | | | | | 0.518 | 0 |

| Pore Radius (r) A | Example 9-6 V (cc/g) | Example 9-6 dV (cc/g) | Example 9-7 V (cc/g) | Example 9-7 dV (cc/g) | Example 8-5 V (cc/g) | Example 8-5 dV (cc/g) |
|---|---|---|---|---|---|---|
| 50 | 0 | 0.088 | 0 | 0.030 | 0 | 0 |
| 150 | 0.088 | 0.292 | 0.030 | 0.020 | 0 | 0 |
| 250 | 0.380 | 0.117 | 0.050 | 0.108 | 0 | 0 |
| 350 | 0.497 | 0.027 | 0.158 | 0.242 | 0 | 0.010 |
| 450 | 0.524 | 0.019 | 0.400 | 0.122 | 0.010 | 0.033 |
| 550 | 0.545 | 0.018 | 0.522 | 0.037 | 0.043 | 0.069 |
| 650 | 0.563 | 0.015 | 0.559 | 0.011 | 0.112 | 0.103 |
| 750 | 0.578 | 0.012 | 0.568 | 0.013 | 0.215 | 0.052 |
| 850 | 0.590 | 0.010 | 0.581 | 0.020 | 0.267 | 0.039 |
| 950 | 0.600 | 0.010 | 0.601 | 0.011 | 0.306 | 0.044 |
| 1050 | 0.610 | 0.008 | 0.612 | 0.005 | 0.350 | 0.045 |
| 1150 | 0.618 | 0.007 | 0.617 | 0.003 | 0.395 | 0.055 |
| 1250 | 0.625 | 0.007 | 0.620 | 0.008 | 0.450 | 0.065 |
| 1350 | 0.632 | 0.005 | 0.628 | 0.015 | 0.515 | 0.037 |
| 1450 | 0.637 | 0.005 | 0.643 | 0.010 | 0.552 | 0.013 |
| 1550 | 0.642 | 0.006 | 0.653 | 0.007 | 0.565 | 0.010 |
| 1650 | 0.648 | 0.004 | 0.660 | 0.009 | 0.575 | 0.005 |
| 1750 | 0.652 | 0.004 | 0.669 | 0.004 | 0.580 | 0.008 |
| 1850 | 0.656 | 0.004 | 0.673 | 0.003 | 0.588 | 0.007 |
| 1950 | 0.660 | 0.015 | 0.026 | 0.026 | 0.595 | 0.028 |
| 2400 | 0.675 | 0.010 | 0.702 | 0.033 | 0.623 | 0.022 |
| 2800 | 0.685 | 0.008 | 0.735 | 0.013 | 0.645 | 0.012 |
| 3200 | 0.693 | 0.007 | 0.748 | 0.002 | 0.657 | 0.008 |
| 3600 | 0.700 | 0.005 | 0.750 | 0.008 | 0.665 | 0.005 |
| 4000 | 0.705 | 0.009 | 0.758 | 0.002 | 0.670 | 0.004 |
| 4400 | 0.714 | | 0.760 | | 0.67 | |

The average pore radius (r) was calculated by the equation below:

$$r = \int_{20}^{\infty} rD(r)\,dr/Vg, \qquad D(r) = \frac{dv}{dr}$$

$$Vg = \int_{20}^{\infty} D(r)\,dr$$

(As to Examples 9-6, 9-7, and 8-5, $r = 20 - 4400\,A$)

The specific surface area, pore volume, pore size distribution, and average pore radius of the catalyst in each run and the results of reaction were as shown in Table 10.

The reaction was performed in the identical manner with Example 1, using 40 g of catalyst. The reaction conditions were, in all runs, as follows: the mol ratio of methanol to phenol, 5.0% WHSV, 0.11 1/hr; and the reaction temperature, 450°C.

Table 11

| Pore radius γ(A) | Example 10-1 V (cc/g) | Example 10-1 dV (cc/g) | Example 9-4 V (cc/g) | Example 9-4 dV (cc/g) |
|---|---|---|---|---|
| 16 | 0 | 0.004 | 0 | 0.030 |
| 25 | 0.004 | 0.163 | 0.030 | 0.230 |
| 75 | 0.167 | 0.051 | 0.260 | 0.185 |
| 125 | 0.218 | 0.069 | 0.445 | 0.060 |
| 175 | 0.287 | 0.097 | 0.505 | 0.023 |
| 225 | 0.384 | 0.041 | 0.528 | 0.007 |
| 275 | 0.525 | 0.365 | 0.535 | 0 |
| 500 | 0.890 | 0.096 | 0.535 | |
| 1000 | 0.986 | 0.050 | 0.535 | |
| 1500 | 1.036 | 0.011 | 0.535 | |
| 2000 | 1.047 | 0.003 | 0.535 | |
| 2500 | 1.050 | 0 | 0.535 | |
| 3000 | 1.050 | 0 | 0.535 | |
| 3500 | 1.050 | 0 | 0.535 | |
| 4000 | 1.050 | 0 | 0.535 | |
| 4400 | 1.050 | | 0.535 | |

The pore volumes and average pore radii of the catalyst of Examples 10-1 and 9-4 are shown in Table 12 below:

Table 10

| Example No. | Calcining Condition (°C.) hr. | Specific Surface Area (m²/g) | Pore Volume (cc/g) | Pore Size Distribution (A) | Average Pore Radius (A) | Reaction Time (hr) | Un-reacted phenol (%) | Yield (%) o-Cresol | Yield (%) 2,6-Xylenol | Yield (%) 2,4,6-Tri-methyl-phenol |
|---|---|---|---|---|---|---|---|---|---|---|
| 9-1 | 550  3 | 78 | 0.33 | 30–120 | 54 | 0–6 | 0 | 0 | 3.0 | 75 |
| | | | | | | 6–24 | 0 | 0 | 6.1 | 80 |
| | | | | | | 24–30 | | | | |
| 9-2 | 400  3 | 107 | 0.43 | 20–290 | 76 | 0–6 | 0 | 0.5 | 2.1 | 72 |
| | | | | | | 6–24 | 0 | 0.6 | 7.7 | 75 |
| 9-3 | | 20 | 0.16 | 50–140 | 80 | 0–6 | 0 | 0.3 | 10 | 58 |
| | | | | | | 6–24 | 0 | 0.2 | 22 | 60 |
| 9-4 | 550  6 | 69 | 0.53 | 20–250 | 85 | 0–6 | 0 | 0 | 2.1 | 78 |
| | | | | | | 6–24 | 0 | 0 | 5.2 | 82 |
| 9-5 | 600  40 | 44 | 0.51 | 60–290 | 132 | 0–6 | 0 | 0.5 | 6.3 | 78 |
| | | | | | | 6–24 | 0 | 0.6 | 9.4 | 76 |
| 9-6 | 700  6 | 25 | 0.71 | 100–4400 | 571 | 0–6 | 0 | 0.5 | 14 | 54 |
| | | | | | | 6–24 | 0 | 1.8 | 18 | 50 |
| 9-7 | 800  6 | 13 | 0.76 | 180–2100 | 775 | 0–6 | 0.1 | 0.1 | 15 | 47 |
| | | | | | | 6–24 | 0.2 | 0.3 | 25 | 36 |
| | | | | | | 0.5 | 1.5 | 29 | 33 | |
| 8-5 | 600  3 / 1000  1 | 11 | 0.67 | 300–4400 | 1180 | 0–6 | 1.3 | 7.0 | 41 | 20 |
| | | | | | | 6–24 | 5.5 | 18 | 43 | 13 |

EXAMPLE 10

This Example is to show the correlation of the preparation method of the catalyst with its specific surface area, break-down strength, and catalytic activity.

EXAMPLE 10-1

The catalyst not pressure-molded

The same magnesium hydroxide as used in Example 9-4 was crushed, and the grains of 5 – 9 mesh were collected by sieving, which were calcined at 550°C. for 6 hours, in the manner similar to Example 9-4.

The catalyst so prepared was extremely weak, and must be handled very gently when packed into the reactor.

The specific surface area, break-down strength, and the results of reaction using the same catalyst were as shown in Table 13, and the pore size distribution in the catalyst was as shown in Table 11. In both Tables the equivalent properties of the pressure-molded catalyst and the reaction results of Example 9-4 are given by way of comparison.

Table 12

| Example No. | Pore Size Distribution (radius, A) | Pore Volume Pores of Radii 20– 225A (cc/g) | Pore Volume Pores of Radii 20 – 4400A (cc/g) | Average Pore Radius (A) |
|---|---|---|---|---|
| 10-1 | 20 – 2500 | 0.38 | 1.05 | 843 |
| 9-4 | 20 – 250 | 0.52 | 0.53 | 85 |

From the results of above Table 12 and later given Table 13, it can be understood that the catalyst not pressure-molded has a large specific surface area and pore volume compared with the pressure-molded catalyst of Example 9-4, but has a small pore volume as to the pores of small radii. The catalyst not pressure-molded furthermore shows a low mechanical strength unpractical for any industrial use, and also rapid deterioration in catalytic activity.

Example 10-2

This Example concerns a magnesium oxide catalyst obtained by calcining a basic magnesium carbonate, which may be formed, for example, through the reaction of a magnesium salt, say, magnesium nitrate, with a carbonate, e.g., sodium carbonate.

A basic magnesium carbonate powder was pressure-molded into the tablets of 6 mm in diameter and 5 mm in thickness, and calcined at 550°C. for 3 hours in an electric oven.

Thus obtained catalyst had an extremely low mechanical strength, and special care must be taken in the handling thereof when it was packed in the reactor.

The specific surface area and break-down strength of the catalyst, as well as the results of reaction using the same catalyst, were as shown in Table 13.

EXAMPLE 10-3

Similarly to Example 1, magnesium oxide powder was violently mixed with water to be converted to magnesium hydroxide, which was pressure-molded into the tablets of 6 mm in diameter and 5 mm in thickness, and calcined in an electric oven at 450°C. for 6 hours.

The specific surface area and break-down strength of the catalyst were as given in Table 13 together with the results of reaction using the same catalyst.

EXAMPLE 10-4

The same tablets of magnesium hydroxide as formed in Example 10-3 were calcined in an electric oven at 600°C. for 6 hours.

The specific surface area and break-down strength of the catalyst were as given in Table 13 together with the results of the reaction using the same catalyst.

EXAMPLE 11

In this Example, various additives were added to magnesium oxide to be used as the catalyst for the subject process.

The catalyst was prepared as follows:

IMPREGNATION METHOD

A mixture of magnesium oxide powder with water was stirred violently to form a gelled magnesium hydroxide. An aqueous solution of the additive was added thereto, and water was evaporated under thorough agitation, leaving a dry system, which was subsequently dried for an overnight in a dryer of 100° – 120°C. The solid was pressure-molded into the tablets of each 6-mm in diameter and 5-mm in thickness, under a pressure of 5 – 6 t/cm². The tablets were sintered in an electric oven at 550°C. for 3 hours.

Note that $B_2O_2$ in Example 11-26 was formed from $B(OH)_3$, $V_2O_5$ in Example 11-39, from ammonium vanadate, and $WO_3$ in Example 11-40, from ammonium p-tungstate. Incidentally, a part or the most of the NaOH employed in Examples 11-1, and 2, was presumably converted in $Na_2CO_3$ during the catalyst preparation.

Blending method

A mixture of magnesium oxide powder and water was violently stirred to form gelled magnesium hydroxide, to which then the additive was added and again stirred violently. Filtering the system, the recovered solid was washed with water, dried for an overnight in a dryer of 100° – 120°C., pressure-molded similarly to the tablet formation in the dipping method, and calcined for 3 hours at 550°C.

Table 13

| Example No. | Specific Surface Area (m²/g) Before Reaction | Specific Surface Area (m²/g) After Reaction | Break-down Strength (kg/cm²) | Reaction Time (hr.) | Yield (%) 2,6-Xylenol | Yield (%) 2,4,6-Tri-methylphenol |
|---|---|---|---|---|---|---|
| 10-1 | 100 | 65 | 0.1 or below | 0–6 | 5.5 | 72 |
|  |  |  |  | 6–24 | 10 | 76 |
|  |  |  |  | 54–72 | 30 | 52 |
| 9-4 | 69 | 61 | 0.9 | 0–6 | 2.1 | 78 |
|  |  |  |  | 6–24 | 5.2 | 82 |
|  |  |  |  | 54–72 | 9.3 | 76 |
| 10-2 | 112 | 59 | 0.1 | 0–6 | 1.8 | 76 |
|  |  |  |  | 6–24 | 4.3 | 80 |
|  |  |  |  | 54–72 | 17 | 66 |
| 10-3 | 153 | 60 | 1.3 | 0–6 | 2.8 | 69 |
|  |  |  |  | 6–24 | 5.6 | 78 |
|  |  |  |  | 54–72 | 14 | 70 |
| 10-4 | 60 | 58 | 1.0 | 0–6 | 2.3 | 80 |
|  |  |  |  | 6–24 | 4.2 | 83 |
|  |  |  |  | 54–72 | 10 | 77 |

In Table 13, the "specific surface area before the reaction" means that of the catalyst before it was used in the methylation reaction, and that "after the reaction" means the specific surface area of the catalyst after it was used for 72 hours in the reaction.

The "break-down strength" is the pressure at which the catalyst tablet was broken, when the pressure was applied from the side of the tablet, i.e., in the direction perpendicular to that of the molding pressure. Ten tablets were selected at random as the test specimen, and the average break-down strength was taken.

Note that ZnO, CaO, SrO, BaO, $Ce_2O_3$, SnO, PbO, and $Fe_2O_3$, which were mixed with magnesium oxide, were the precipitates formed upon adding aqueous ammonia to the aqueous solution of nitrates of the named metals. Also $TiO_2$, $ZrO_2$, and $UO_3$ were the precipitates formed upon addition of aqueous ammonia to the aqueous solutions of, respectively, $TiOSO_4$, $ZrO(NO_3)_2$, and $UO_2(NO_3)_2$. The $CaCO_3$ and $BaCO_3$ were the precipitates formed upon mixing ammonium carbonate with the aqueous solutions of, respectively $Ca(NO_3)_2$ and $Ba(NO_3)_2$. The $CaSO_4$ and $BaSO_4$ were the precipitates formed upon mixing ammonium sulfate with the aqueous solutions of, respectively, $Ca(NO_3)_2$ and $Ba(NO_3)_2$. The $Ca_3(PO_4)_2$, $Mg_3(PO_4)_2$, $AlPO_4$ and $FePO_4$ were formed by mixing aqueous solutions of nitrates of the respective metals, i.e., Ca, Mg, Al, and Fe, with an aqueous solution of diammonium hydrogenphosphate, and adjusting the pH to each predetermined value. The tertiary salts whereupon precipitated were recovered and mixed with the magnesium hydroxide. The borates such as $CaB_4O_7$, $Al_2B_2O_6$, and $MnB_4O_7$ were those commercially available, which were finely divided and mixed with slurry-formed magnesium hydroxide under violent agitation. The $SiO_2$ was a 20 wt % (as $SiO_2$) silica sol, and $Al_2O_3$ was a 10 wt % (as $Al_2O_3$) alumina sol.

Precipitation method

To a mixed aqueous solution of nitrate of the metal to be added and magnesium nitrate, aqueous ammonia was added, and the formed precipitate was washed with water, filtered, and dried in a dryer at 100° – 120°C. Thus obtained solid was pressure-molded into the tablets similarly to the case of dipping method. The tablets were calcined at 550°C. for 3 hours.

The reaction was performed at 450°C. under atmospheric pressure, at the WHSV of 0.11 1/hr, and at the methanol-to-phenol mol ratio of 5.0, in the manner similar to Example 1. The results were as shown in Table 14.

From the same Table, it can be understood that when basic compounds were added to the magnesium oxide catalyst, side-formation of meta-methylated phenols such as 2,3,6-trimethylphenol, 2,3,5-trimethylphenol, 2,4,5-trimethylphenyl, and 2,3,4,6-tetramethylphenol was advantageously reduced. Particularly the addition of sodium hydroxide in Example 11-2, sodium carbonate in Example 11-3, dibasic sodium phosphate in Example 11-4, sodium borate in Example 11-7, water glass in Example 11-8, and sodium aluminate in Example 11-9, was effective to reduce the formation of meta-methylated phenols, and to maintain the high activity and prolong the lift of the catalyst.

Also the boron compounds and phosphates contributed to increase the mechanical strength of the catalyst. Particularly when boron oxide and borates of manganese, aluminum, sodium and calcium as shown in the Examples were added, the increase in the catalyst's mechanical strength was conspicuous.

Table 14

| Example No. | Additive | Wt. Ratio of Additive to MgO | Method of Catalyst Preparation | Specific Surface Area (m²/g) Before Reaction | After Reaction (reaction time/hr.) | Recovered phenol (%) | o-Cresol (%) | 2,4-Xylenol (%) | 2,6-Xylenol (%) | Yield 2,3,6-, 2,3,5-, and 2,4,5-Trimethylphenols (%) | 2,4,6-Trimethylphenol (%) | 2,3,4,6-Tetramethylphenol (%) |
|---|---|---|---|---|---|---|---|---|---|---|---|---|
| 11-1 | NaOH | 0.001 | impregnation | 73 | 49 (48) | 0 | 0.5 | 6.5 | 6.2 | 0.8 | 73 | 1.0 |
| 11-2 | NaOH | 0.01 | " | 93 | 54 (48) | 0 | 0.2 | 3.0 | 4.3 | 1.8 | 78 | 0.9 |
| 11-3 | $Na_2CO_3$ | 0.025 | " | 66 | 60 (78) | 0 | 1.0 | 3.1 | 8.3 | 0.8 | 74 | 0.2 |
| 11-4 | $Na_2HPO_4$ | 0.05 | " | 57 | 50(126) | 0 | 0 | 0.4 | 2.0 | 0.6 | 83 | 0.5 |
| 11-5 | $Na_2SO_4$ | 0.05 | " | 45 | 36 (24) | 0 | 0 | 0.8 | 7.1 | 0.3 | 70 | 0.5 |
| 11-6 | NaCl | 0.05 | " | 25 | 25 (30) | 0 | 0 | 0.3 | 23 | 0.7 | 61 | 0.7 |
| 11-7 | $Na_2B_4O_7$ | 0.03 | " | 63 | 54 (72) | 0 | 0.9 | 3.7 | 5.1 | 1.1 | 79 | 0.6 |
| 11-8 | $Na_2O \cdot 3SiO_2$ | 0.03 | " | 69 | 61 (72) | 0 | 0 | 0.4 | 2.0 | 0.4 | 81 | 0.8 |
| 11-9 | $NaAlO_2$ | 0.01 | " | 77 | 64 (78) | 0 | 0 | 1.5 | 2.9 | 1.0 | 80 | 0.5 |
| 11-10 | $NaBiO_3$ | 0.02 | " | 67 | 57 (48) | 0 | 0 | 0.8 | 7.5 | 0.6 | 74 | 0.3 |
| 11-11 | $Li_2CO_3$ | 0.025 | " | 49 | 43 (24) | 0 | 0 | 1.6 | 11.9 | 0.6 | 68 | 0.6 |
| 11-12 | $K_2CO_3$ | 0.025 | " | 50 | 43 (24) | 0 | 0 | 5.8 | 13.0 | 0.2 | 67 | trace |
| 11-13 | $Mg_3(PO_4)_2$ | | Blending | 63 | 55 (78) | 0 | 0 | 0.8 | 8.2 | 1.0 | 77 | 1.1 |
| 11-14 | $MgSO_4$ | 0.03 | Impregnation | 54 | 52 (30) | 0 | 0 | 0.4 | 13.0 | 3.1 | 58 | 6.2 |
| 11-15 | $ZnSO_4$ | 0.03 | " | 61 | 45 (30) | 0 | 0 | 0.5 | 18.0 | 1.7 | 61 | 3.8 |
| 11-16 | ZnO | 0.03 | Blending | 63 | 50 (24) | 0 | 0 | 1.1 | 10.3 | 0.9 | 69 | 1.3 |
| 11-17 | CaO | 0.05 | " | 34 | 33 (24) | 0 | 0 | 1.3 | 9.4 | 0.4 | 63 | 0.4 |
| 11-18 | $Ca_3(PO_4)_2$ | | " | 67 | 58 (78) | 0 | 0 | 0.9 | 5.7 | 0.9 | 80 | 1.3 |
| 11-19 | $CaCO_3$ | 0.03 | " | 41 | 39 (48) | 0 | 0 | 0.6 | 5.3 | 1.3 | 69 | 1.4 |
| 11-20 | $CaSO_4$ | 0.03 | " | 62 | 57 (24) | 0 | 0 | 0.8 | 3.6 | 1.2 | 78 | 3.3 |
| 11-21 | $CaB_4O_7$ | 0.05 | " | 54 | (24) | 0 | 0 | 0.3 | 7.8 | 1.3 | 65 | 7.3 |
| 11-22 | SrO | 0.05 | " | 55 | 48 (24) | 0 | 0 | 1.1 | 11.5 | 1.0 | 68 | 1.5 |
| 11-23 | BaO | 0.05 | " | 60 | 51 (48) | 0 | 0 | 1.5 | 7.9 | 0.5 | 79 | 1.2 |
| 11-24 | $BaSO_4$ | 0.03 | " | 58 | 49 (24) | 0 | 0 | 0.7 | 4.7 | 1.4 | 78 | 2.5 |
| 11-25 | $BaCO_3$ | 0.03 | " | 44 | 40 (30) | 0 | 0 | 1.7 | 8.8 | 0.8 | 79 | 1.3 |
| 11-26 | $B_2O_3$ | 0.03 | Impregnation | 79 | 71 (24) | 0 | 0 | 0.6 | 21 | 3.3 | 49 | 7.4 |
| 11-27 | $Al_2O_3$ | 0.03 | Blending | 75 | 70 (24) | 0 | 0 | 0.9 | 4.6 | 2.1 | 73 | 2.5 |
| 11-28 | $AlPO_4$ | 0.05 | " | 72 | 72 (24) | 0 | 0 | 0.3 | 4.7 | 1.3 | 76 | 8.9 |
| 11-29 | $Al_2(SO_4)_3$ | 0.05 | Impregnation | 45 | 43 (24) | 0 | 0 | 2.2 | 14.3 | 4.4 | 47 | 10.2 |
| 11-30 | $Al_2B_2O_6$ | 0.05 | Blending | 68 | 59 (78) | 0 | 0 | 1.0 | 2.6 | 2.6 | 69 | 15.3 |
| 11-31 | $Ce_2O_3$ | 0.03 | " | 42 | 33 (24) | 0 | 0 | 0.7 | 29.1 | 1.9 | 48 | 3.9 |
| 11-32 | $SiO_2$ | 0.10 | " | 130 | 128 (24) | 0 | 0.6 | 1.4 | 1.8 | 4.1 | 50 | 16.4 |
| 11-33 | $SiO_2$ | 0.03 | " | 98 | 73 (48) | 0 | 0 | 0.7 | 3.2 | 2.5 | 79 | 2.7 |
| 11-34 | SnO | 0.03 | " | 58 | 53 (24) | 0 | 0 | 0.7 | 5.8 | 2.6 | 64 | 2.9 |
| 11-35 | PbO | 0.03 | " | 55 | 50 (24) | 0 | 0 | 3.2 | 4.0 | 1.3 | 59 | 4.6 |
| 11-36 | $TiO_2$ | 0.03 | " | 75 | 62 (48) | 0 | 0 | 1.1 | 3.7 | 2.1 | 78 | 3.2 |
| 11-37 | $ZrO_2$ | 0.10 | " | 100 | 70 (48) | 0.1 | 0.8 | 4.8 | 4.2 | 2.9 | 58 | 5.7 |
| 11-38 | $ZrO_2$ | 0.03 | " | 79 | 65 (48) | 0 | 0 | 2.6 | 2.8 | 1.8 | 77 | 2.9 |
| 11-39 | $V_2O_5$ | 0.03 | Impregnation | 57 | 52 (48) | 0 | 0.7 | 2.3 | 4.5 | 1.3 | 68 | 2.0 |
| 11-40 | $WO_3$ | 0.03 | Precipitation | 123 | 72 (48) | 0 | 0 | 2.3 | 1.8 | 1.1 | 79 | 4.4 |
| 11-41 | $MnB_4O_7$ | 0.03 | Blending | 93 | | 0 | 0 | 0.6 | 12.1 | 2.0 | 63 | 4.4 |
| 11-42 | $FePO_4$ | 0.05 | " | 60 | 59 (24) | 1.0 | 6.4 | 2.7 | 7.8 | 4.8 | 48 | 8.8 |
| 11-43 | $Fe_2(SO_4)_3$ | 0.05 | Impregnation | 85 | 57 (24) | 0 | 2.3 | 10.6 | 16.5 | 1.8 | 58 | 1.2 |
| 11-44 | $NiSO_4$ | 0.05 | " | 115 | 60 (24) | 0 | 2.0 | 8.5 | 10.5 | 1.9 | 52 | 1.7 |

Table 14-continued

| Example No. | Additive | Wt. Ratio of Additive to MgO | Method of Catalyst Preparation | Specific Surface Area (m²/g) Before Reaction | After Reaction (reaction time/hr.) | Recovered phenol (%) | o-Cresol (%) | 2,4-Xylenol (%) | 2,6-Xylenol (%) | Yield 2,3,6-, 2,3,5-, and 2,4,5-, Trimethylphenols (%) | 2,4,6-Trimethylphenol (%) | 2,3,4,6-Tetramethylphenol (%) |
|---|---|---|---|---|---|---|---|---|---|---|---|---|
| 11-45 | UO₃ | 0.03 | Blending | 53 | 46 (24) | 0 | 6.4 | 17.9 | 7.4 | 0.9 | 53 | 0.3 |
| 11-46 | ThO₂ | 0.03 | " | 57 | 43 (24) | 0 | 3.8 | 0.3 | 10.0 | 2.2 | 61 | 7.4 |

EXAMPLE 12

This Example is to illustrate the correlation of the method of making the catalyst with its break-down strength.

EXAMPLE 12-1

The 20 – 100 mesh magnesium hydroxide obtained by violently stirring magnesium oxide powder with water was molded into tablets of 6 mm in diameter and 5 mm in thickness, under a molding pressure of 5 – 6 t/cm². The tablets were calcined at 600°C. for 3 hours.

EXAMPLE 12-2

The magnesium hydroxide tablets obtained in Example 12-1 were pulverized and the grains of 20 – 100 mesh were collected, and pressure-molded similarly to Example 12-1. The tablets were calcined at 600°C. for 3 hours.

EXAMPLE 12-3

The magnesium oxide of 20 – 100 mesh in size having a specific surface area of 73 m²/g, pore volume of 0.56 cc/g, and a pore size distribution of 20 – 200 A, was pressure-molded similarly to Example 12-1.

EXAMPLE 12-4

The same magnesium oxide as employed in Example 12-3 was pressure-molded under a pressure of 1 – 1.2 t/cm², crushed, and the grains of 20 – 100 mesh in size were collected and pressure-molded in the identical manner with Example 12-1.

EXAMPLES 12-5 through 10

The same magnesium oxide as employed in Example 12-3 was pulverized, and the powder was blended, by means of a mixer, with respectively stearic acid (Example 12-5), calcium tertiary phosphate (Example 12-6), calcium secondary phosphate (Example 12-7), manganese borate (Example 12-8), aluminum borate (Example 12-9), and calcium borate (Example 12-10). Each mixture was molded under a pressure of 1 – 1.2 t/cm², crushed, the grains of 20 – 100 mesh in size were collected, and again pressure-molded in the identical manner with Example 12-1.

The break-down strengths of the foregoing catalysts and some of those prepared in Example 11 were tested similarly to Example 10. The results were as given in Table 15.

The catalysts of Examples 12-1 through 10 were used in the methylation of phenol at the reaction temperature of 450°C., pressure of 1 atm., WHSV of 0.11 1/hr., and the mol ratio of methanol to phenol of 5.0. The results of the reaction during 6 to 24 hours' run were also given in Table 15.

Table 15

| Example No. | Additive | Wt. Ratio of Additive to MgO | Break-down Strength After Molding (kg/cm²) | After Sintering (kg/cm²) | Yield (%) 2,6-Xylenol | 2,4,6-Trimethylphenol |
|---|---|---|---|---|---|---|
| 12-1 | — | — | 3.0 | 0.8 | 4.8 | 82 |
| 12-2 | — | — | 5.7 | 2.1 | 5.1 | 81 |
| 12-3 | — | — | 7.1 | * | 5.2 | 81 |
| 12-4 | — | — | 8.2 | * | 5.5 | 80 |
| 12-5 | Stearic acid | 0.05 | 17.3 | 2.6 | 6.9 | 76 |
| 12-6 | Ca₃(PO₄)₂ | 0.05 | 9.2 | * | 3.8 | 81 |
| 12-7 | CaHPO₄ | 0.05 | 9.1 | * | 3.5 | 75 |
| 12-8 | MnB₄O₇ | 0.05 | 10.4 | * | 5.4 | 78 |
| 12-9 | Al₂B₂O₆ | 0.05 | 9.9 | * | 2.1 | 74 |
| 12-10 | CaB₄O₇ | 0.05 | 8.9 | * | 6.2 | 73 |

Note : In the table, * mark denotes that no calcining treatment was given.

From the results shown in Table 15, it can be understood that particularly the phosphates and borates are useful as the assisting agents of molding.

The catalysts of Examples 12-3, 4, 5, 6, 7, 8, 9, and 10 were those formed by molding magnesium oxide, which were useful as the catalysts as they were. Whereas, those of Examples 12-1 and 2, and 11-6, 10, 26, 31, 47 and 51 were formed by molding magnesium hydroxide, and should preferably be calcined under appropriate conditions. In the latter cases, the break-down strength of the catalysts was reduced by the calcining. In order to avoid the breaking down of the catalysts during their filling operation into the reactor, the molded catalyst before calcining may be packed into the reactor, and calcined in situ.

EXAMPLE 13

In the preparation of 2,4,6-trimethylphenol by contacting phenol and methanol with catalyst, the catalytic activity gradually decreases. This Example demonstrates the regeneration of such used catalyst having a reduced catalytic activity.

The process of this invention was practiced using the magnesium oxide catalyst prepared by the same method under identical conditions with those of Example 9–4, in the manner similar to Example 1. The mol ratio of methanol to phenol in the starting material was 5.0, the reaction temperature was 450°C., the pressure was 1 atmosphere and WHSV was 0.11 l/hr. The catalyst of which activity was deteriorated after a prolonged use in the above reaction was left as filled in the reaction tube after the reaction ended, and through which nitrogen gas was passed at 450°C. for an hour to substitute the atmosphere. Thereafter air was introduced thereinto at a flow rate of 0.10 l/min. (standard state), and also water, at a flow rate of 20 g/hr. (the gaseous composition: $O_2 = 3.9$ vol %, $N_2 = 15.5$ vol %, and $H_2O = 80.6$ vol %). The catalyst bed was maintained at 480° – 500°C., and treated for 3.5 hours. Upon the sintering treatment the black catalyst of reduced activity became white. During the treatment, formation of carbon dioxide gas was observed.

The foregoing reaction and catalyst's regeneration were alternatively repeated, with the results as given in Table 16.

Table 16

| Reaction Time (hr.) | 2,4,6-Trimethylphenol Yield (%) | 2,6-Xylenol Yield (%) |
|---|---|---|
| 0 – 24 | 78 | 2 |
| 24 – 48 | 80 | 6 |
| 48 – 72 | 77 | 10 |
| 72 – 96 | 72 | 14 |
| 96 – 120 | 66 | 18 |
| 120 – 144 | 63 | 20 |
| Regenerating Treatment | | |
| 0 – 24 | 76 | 2 |
| 24 – 48 | 78 | 7 |
| 48 – 72 | 73 | 12 |
| 72 – 96 | 65 | 16 |
| 96 – 120 | 60 | 21 |
| 120 – 144 | 56 | 24 |
| Regenerating Treatment | | |
| 0 – 24 | 76 | 3 |
| 24 – 48 | 79 | 5 |
| 120 – 144 | 57 | 26 |
| Regenerating Treatment | | |
| 0 – 24 | 77 | 2 |

Table 16-continued

| Reaction Time (hr.) | 2,4,6-Trimethylphenol Yield (%) | 2,6-Xylenol Yield (%) |
|---|---|---|
| 24 – 48 | 80 | 7 |
| 120 – 144 | 54 | 27 |
| Regenerating Treatment | | |
| 0 – 24 | 75 | 3 |
| 24 – 48 | 77 | 6 |
| 120 – 144 | 56 | 22 |
| Regenerating Treatment | | |
| 0 – 24 | 76 | 3 |
| 24 – 48 | 79 | 5 |
| 120 – 144 | 55 | 26 |

From the results of Table 16, it can be understood that the catalyst shows substantially no reduction in its activity after 5 repetitive regeneration treatment.

The catalyst thus regenerated 5 times and used in the total of 36 days' reaction was regenerated the 6th time under the identical conditions. The catalyst was then withdrawn from the reaction tube and measured of the specific surface area, pore volume, pore size distribution and average pore radius. The results were as follows:

| | |
|---|---|
| Specific surface area | 54 m²/g |
| Pore volume | 0.61 cc/g |
| Pore size distribution | 30 – 2400 A |
| Average pore radius | 184 A |

The particulars of the pore size distribution were as in the Table below:

Table 17

| Pore Radius (A) | Pore Volume V (cc/g) | Pore Volume dV (cc/g) | Pore Radius (A) | Pore Volume V (cc/g) | Pore Volume dV (cc/g) |
|---|---|---|---|---|---|
| 25 | 0 | 0.006 | 325 | 0.565 | 0.002 |
| 35 | 0.006 | 0.008 | 335 | 0.567 | 0.002 |
| 45 | 0.014 | 0.014 | 345 | 0.569 | 0.007 |
| 55 | 0.028 | 0.022 | 450 | 0.576 | 0.016 |
| 65 | 0.050 | 0.035 | 550 | 0.592 | 0.008 |
| 75 | 0.085 | 0.050 | 650 | 0.600 | 0.001 |
| 85 | 0.135 | 0.055 | 750 | 0.601 | 0.002 |
| 95 | 0.190 | 0.053 | 850 | 0.603 | 0.002 |
| 105 | 0.243 | 0.047 | 950 | 0.605 | 0.001 |
| 115 | 0.290 | 0.048 | 1050 | 0.606 | 0.002 |
| 125 | 0.338 | 0.037 | 1400 | 0.608 | 0.002 |
| 135 | 0.375 | 0.027 | 1800 | 0.610 | 0.003 |
| 145 | 0.402 | 0.036 | 2200 | 0.613 | 0.002 |
| 155 | 0.438 | 0.027 | 2600 | 0.615 | 0 |
| 165 | 0.465 | 0.023 | 3000 | 0.615 | |
| 175 | 0.488 | 0.009 | 3400 | 0.615 | |
| 185 | 0.497 | 0.009 | | | |
| 195 | 0.508 | 0.011 | | | |
| 205 | 0.519 | 0.007 | | | |
| 215 | 0.526 | 0.009 | | | |
| 225 | 0.535 | 0.005 | | | |
| 235 | 0.540 | 0.005 | | | |
| 245 | 0.545 | 0.003 | | | |
| 255 | 0.548 | 0.004 | | | |
| 265 | 0.552 | 0.003 | | | |
| 275 | 0.555 | 0.002 | | | |
| 285 | 0.557 | 0.003 | | | |
| 295 | 0.560 | 0.002 | | | |
| 305 | 0.562 | 0.004 | | | |
| 315 | 0.564 | 0.001 | | | |

EXAMPLE 14

In this Example, the catalyst of reduced activity was regenerated by a calcining treatment in the atmosphere of gaseous mixture of oxygen and nitrogen, while in Example 13 the same object was achieved by the calcining treatment in the presence of water.

The magnesium oxide catalyst prepared by the same method under identical conditions as of Example 9–4 was used in the methylation reaction similar to that of Example 13 under identical conditions. The catalyst of which activity was reduced was left as it was in the reaction tube, and after the reaction was terminated, nitrogen gas was passed through the reaction tube for an hour at 80 450°C. to substitute the inside atmosphere. Thereafter a gaseous mixture composed of air at a flow rate of 0.10 l/min., and nitrogen gas at a flow rate of 0.41 l/min. (both calculated as in the standard state) (composition of the gas: $O_2 = 3.9$ vol. %, and $N_2 = 96.1$ vol %) was introduced into the reaction tube. Thus the catalyst bed was treated for 3.5 hours while maintained at 480° – 500°C.

The results of repeating the foregoing methylation reaction and the catalyst's regeneration were as shown in Table 18 below.

Table 18

| Reaction Time (hr.) | 2,4,6-Trimethylphenol Yield (%) | 2,6-Xylenol Yield (%) |
|---|---|---|
| 0 – 24 | 76 | 2 |
| 24 – 48 | 79 | 5 |
| 48 – 72 | 78 | 8 |
| 72 – 96 | 74 | 12 |
| 96 – 120 | 69 | 15 |
| 120 – 144 | 64 | 18 |
| Regenerating Treatment | | |
| 0 – 24 | 73 | 3 |
| 24 – 48 | 74 | 8 |
| 48 – 72 | 70 | 13 |
| 72 – 96 | 63 | 18 |
| 96 – 120 | 58 | 23 |
| 120 – 144 | 53 | 26 |
| Regenerating Treatment | | |
| 0 – 24 | 69 | 4 |
| 24 – 48 | 75 | 8 |
| 120 – 144 | 50 | 29 |
| Regenerating Treatment | | |
| 0 – 24 | 68 | 5 |
| 24 – 48 | 72 | 10 |
| 120 – 144 | 47 | 32 |
| Regenerating Treatment | | |
| 0 – 24 | 66 | 4 |
| 24 – 48 | 73 | 9 |
| 120 – 144 | 46 | 32 |
| Regenerating Treatment | | |
| 0 – 24 | 65 | 6 |
| 24 – 48 | 70 | 10 |
| 120 – 144 | 47 | 31 |

EXAMPLE 15

In this Example, the catalyst of reduced activity was regenerated under various conditions:

The magnesium oxide catalyst prepared in the same manner under identical conditions as of Example 9–4 was used in the methylation reaction under the identical conditions as of Example 13. After the reaction ended, the catalyst bed was left in the reaction tube and through which nitrogen gas was passed for an hour at 450°C. to substitute the inside atmosphere. Then the catalyst's regeneration was effected under various conditions as follows:

EXAMPLE 15–1

Air and water were introduced into the reaction tube at a respective flow rate of 0.10 l/min. (standard state) and 20 g/hr. (feed rate of the gas = 0.51 l/min. at standard state; composition of the gas: $O_2 = 3.9$ vol %, $N_2 = 15.5$ vol %, and $H_2O = 80.6$ vol %). The catalyst bed was maintained at 600° – 650°C. and treated for 2 hours and 20 minutes.

EXAMPLE 15–2

The regeneration conditions were the same to those of Example 15–1. The catalyst bed was maintained at 410° – 430°C. and treated for 9 hours.

EXAMPLE 15–3

The regeneration conditions were the same to those of Example 15–1. The catalyst bed was maintained at 200°C. and treated for 24 hours, but substantially no combustion of the carbon and the like adhered onto the catalyst was observed.

EXAMPLE 15–4

The catalyst was treated with air and nitrogen gas at the respective flow rate of 0.10 l/min. (standard state) and 0.41 l/min., at 440° – 460°C. for 5 hours, and then the temperature was lowered to 150°C. At said temperature, the catalyst was further treated for 5 hours with water at a flow rate of 30 g/hr. (steam flow rate: 0.62 l/min. at the standard state), and for additional 6 hours at 450°C. with nitrogen gas at a flow rate of 0.2 l/min.

The results of repeating the foregoing methylation reaction and the catalyst regenerating treatment were as given in Table 19 below:

Table 19

| Example No. | 15-1 | | 15-2 | | 15-3 | | 15-4 | |
|---|---|---|---|---|---|---|---|---|
| Reaction Time (hr.) | 2,4,6-Trimethyl-phenol Yield (%) | 2,6-Xylenol Yield (%) | 2,4,6-Trimethyl-phenol Yield (%) | 2,6-Xylenol Yield (%) | 2,4,6-Trimethyl-phenol Yield (%) | 2,6-Xylenol Yield (%) | 2,4,6-Trimethyl-phenol Yield (%) | 2,6-Xylenol Yield (%) |
| 0 – 24 | 75 | 2 | 75 | 2 | 77 | 3 | 78 | 1 |
| 24 – 48 | 81 | 5 | 80 | 4 | 80 | 5 | 82 | 4 |
| 120 – 144 | 59 | 22 | 61 | 20 | 60 | 23 | 63 | 19 |
| Regenerating Treatment | | | | | | | | |
| 0 – 24 | 62 | 18 | 75 | 13 | 56 | 25 | 72 | 2 |
| 24 – 48 | 56 | 24 | 79 | 6 | 55 | 27 | 81 | 5 |
| 120 – 144 | | | 57 | 24 | 39 | 35 | 59 | 22 |
| Regenerating Treatment | | | | | | | | |
| 0 – 24 | — | — | 76 | 3 | — | — | 74 | 2 |
| 24 – 48 | — | — | 80 | 5 | — | — | 80 | 5 |
| 120 – 144 | — | — | 55 | 26 | — | — | 60 | 20 |

We claim:

1. A process for the preparation of 2,4,6-trimethylphenol by reacting a phenolic compound of the formula:

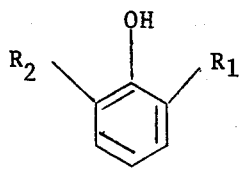

(1)

in which $R_1$ and $R_2$ each stands for hydrogen atom or methyl group, with methanol at vapor phase to methylate the former, which comprises performing the reaction at a temperature in range of from 430° –475°C., the gaseous mixture being composed essentially of the phenolic compound and methanol being contacted at a flow rate not higher than 0.4/hour, calculated as the sum weight in grams of the phenol and methanol per catalyst's weight in grams/hour, with a catalyst of which at least 90% by weight consists of magnesium oxide, said catalyst containing (1) no acidic substance of acid strength of pKa 4.8 or below and no basic substance of base strength of pKa 18.4 or above, and having (2) the ratio of basicity (k) of 60 to 100% wherein:

$$\left[ k = \frac{\text{Amount of base}}{\text{amount of base} + \text{amount of acid}} \times 100 \,(\%), \right]$$

and (3) a specific surface area of at least 15 m²/g.

2. The process for the preparation of 2,4,6-trimethylphenol according to claim 1, in which the gaseous mixture composed essentially of the phenol and methanol is contacted with the catalyst at a flow rate ranging from 0.1 to 0.2/hour.

3. The process for the preparation of 2,4,6-trimethylphenol according to claim 1, in which the gaseous mixture composed essentially of the phenol and methanol is contacted with the catalyst at a flow rate ranging from 0.04 to 0.15/hour.

4. The process according to claim 1, in which the reaction is performed at the temperatures ranging from 420° to 490°C.

5. The process according to claim 1, in which the reaction is performed at the temperatures higher than 430°C. but lower than 475°C.

6. The process according to claim 1, in which the phenol and methanol are diluted with an inert gas and used for the reaction.

7. The process according to claim 6, in which the inert gas is steam.

8. The process according to claim 7, in which not more than 10 mols of water per mol of the phenol is used, and the phenol and methanol are diluted with the steam formed from said water.

9. The process according to claim 1, in which the methanol is used, based on the theoretical mol number of the methyl groups to be introduced into a mol of phenol to form 2,4,6-trimethylphenol, in the amount of 0.5 – 5 times the theoretical mol number per mol of phenol.

10. The process according to claim 1, in which the reaction is performed at the pressures ranging from 0.5 to 20 atmospheric pressures, as absolute pressure.

11. The process according to claim 1, in which the reaction is performed at the pressures ranging from 1 to 16 atmospheric pressures, as absolute pressure.

12. The process according to claim 1, in which the magnesium oxide has a pore radius (r) of 20 – 400 A is used as the catalyst.

13. The process according to claim 1, in which the magnesium oxide has a pore radius (r) of 30 – 150 A is used as the catalyst.

14. The process according to claim 1, in which at least one metallic compound selected from the group consisting of hydroxide, carbonate, phosphate, borate, silicate, aluminate of alkali metals and oxide, carbonate, phosphate, borate, of alkaline earth metals, is added to the magnesium oxide to serve as the catalyst.

15. The process according to claim 14, in which at most 10% by weight to the magnesium oxide of the metallic compound is added to the magnesium oxide to serve as the catalyst.

16. The process according to claim 14, in which up to 5% by weight to the magnesium oxide of the metallic compound is added to the magnesium oxide to serve as the catalyst.

17. The process according to claim 1, in which the phenolic compound is phenol containing no methyl substituent group, which is expressed by the formula,

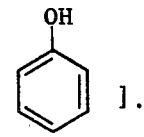

].

18. The process according to claim 1, in which the magnesium oxide-containing catalyst of which activity has been reduced is subjected to an oxidation treatment comprising contacting the catalyst with molecular oxygen or a molecular oxygen-containing gas at the temperatures ranging from 200° to 700°C., and the thus regenerated catalyst is used in the methylation of phenol.

19. The process according to claim 1, in which the magnesium oxide-containing catalyst of which activity has been reduced is subjected to an oxidation treatment comprising contacting the catalyst with molecular oxygen or a molecular oxygen-containing gas at temperatures ranging from 200° to 700°C., and then to a water treatment comprising contacting the catalyst with water or steam at the temperatures ranging from the normal to 650°C., and the thus regenerated catalyst is used in the methylation of phenol.

20. The process according to claim 1, in which the magnesium oxide-containing catalyst of which activity has been reduced is contacted with molecular oxygen or a molecular oxygen-containing gas at the temperatures ranging from 200° to 600°C., in the presence of water or steam, and the thus regenerated catalyst is used in the methylation of phenol.

* * * * *

UNITED STATES PATENT AND TRADEMARK OFFICE
CERTIFICATE OF CORRECTION

PATENT NO. : 3,968,172
DATED : July 6, 1976
INVENTOR(S) : Yataro Ichikawa et al.

It is certified that error appears in the above-identified patent and that said Letters Patent are hereby corrected as shown below:

Claim 17, line 2, delete "containing no methyl", insert -- . --

Claim 17, delete line 3 and the formula in their entirety.

Signed and Sealed this

Fifth Day of October 1976

[SEAL]

Attest:

RUTH C. MASON
Attesting Officer

C. MARSHALL DANN
Commissioner of Patents and Trademarks